United States Patent [19]
Korsmeyer

[11] Patent Number: 5,856,445
[45] Date of Patent: Jan. 5, 1999

[54] SERINE SUBSTITUTED MUTANTS OF BCL-$X_L$/BCL-2 ASSOCIATED CELL DEATH REGULATOR

[75] Inventor: Stanley J. Korsmeyer, Clayton, Mo.

[73] Assignee: Washington University, St. Louis, Mo.

[21] Appl. No.: 733,505

[22] Filed: Oct. 18, 1996

[51] Int. Cl.[6] .................................................. C07K 14/00
[52] U.S. Cl. ......................................... 530/350; 435/69.1
[58] Field of Search ............................ 530/350; 435/69.1

[56] References Cited

PUBLICATIONS

Oltavi and Korsmeyer, Checkpoints of Dueling Dimers Foil Death Wishes, *Cell* 79:189–192, 1994.

Bakhshi et al., Cloning the Chromosomal Breakpoint of t(14;18) Human Lymphomas: Clustering around $J_H$ on Chromosome 14 and near a Transcriptional Unit on 18, *Cell* 41:899–906, 1985.

Tsujimoto et al., The t(14;18) Chromosome Translocations Involved in B–Cell Neoplasms Result from Mistakes in VDJ Joining, *Science* 229:1390–1393, 1985.

Cleary and Sklar, Nucleotide sequence of a t(14;18) chromosomal breakpoint in follicular lymphoma and demonstration of a breakpoint–cluster region near a transcriptionally active locus on chromosome 18, *Proc. Natl. Acad. Sci. USA* 82:7439–7443, 1985.

Korsmeyer, Bcl–2 Initiates a New Category of Oncogenes: Regulators of Cell Death, *Blood* 80:879–886, 1992.

Yin et al., BH1 and BH2 domains of Bcl–2 are Required for Inhibition of Apoptosis and Heterodimerization with Bax, *Nature* 369:321–323, 1994.

Boyd et al., Bik, a novel death–inducing protein shares a distinct sequence motif with Bcl–2 family proteins and interacts with viral and cellular survival–promoting proteins, *Oncogene* 11:1921–1928, 1995.

Chittenden et al., A conserved domain in Bak, distinct from BH1 and BH2, mediates cell death and protein binding functions, *Embo. J.* 14:5589–5596, 1995.

Farrow and Brown, New Members of the Bcl–2 Family and their Protein Partners, *Curr. Opin. Genet. Dev.* 6:45–49, 1996.

Oltvai et al., Bcl–2 Heterodimerizes In Vivo with a Conserved Homolog, Bax, that Accelerates Programmed Cell Death, *Cell* 74:609–619, 1993.

Yang et al., Bad, A Heteroclimeric Partner For Bcl–xL & Bcl–2, Displaces Bax & Promotes Cell death, *Cell* 80:285–291, 1995.

Muslin et al., Interaction of 14–3–3 with Signaling Proteins is Mediated by the Recognition of Phosphoserine, *Cell* 84:889–897, 1996.

Furukawa et al., *Biochem. Biophys. Res. Comm.* 194:144–149, 1993.

Cross et al, Purification of CpG islands using a methylated DNA binding column, *Nature Genet.* 6:236–244, 1994.

Cohen, The Structure and Regulation of Protein Phosphatases, *Ann. Rev. Biochem.* 58:453–508, 1989.

Wera and Hemmings, Serine/threonine protein phosphatases, *Biochem. J.* 311:17–29, 1995.

Shenolikar, Protein phosphatase regulation by endogenous inhibitors, *Cancer Biol.* 6:219–227,1995.

Matthews, Protein Kinases and Phosphatases that act on Histidine, Lysine, or Arginine Residues in Eukaryotic Proteins: A Possible Regulator of the Mitogen–activated Protein Kinase Cascade, *Pharmac. Ther.* 67:323–350, 1995.

Levitski, Signal–transduction therapy, *Eur. J. Biochem.* 226:1–13, 1994.

BLAST Search Accession No. Z57098, Oct. 18, 1995.

BLAST Search Accession No. Z57099, Oct. 18, 1995.

Sambrook et al Molecular Cloning: A Laboratory Manual Second Edition vol. 2 Chapter 15, 1989.

Lazar et al Molecular adn Cellular Biology vol. 8 No. 3 1247–1252, Mar. 1988.

Burgess et al Journal of Cell biology vol. 111 2129–2138., Nov. 1990.

Schwartz et al Proc Natl Acad Sci USA vol. 84 6408–6411, Sep. 1987.

Lin et al Biochemistry vol. 14 No. 8 1559–1563, 1975.

*Primary Examiner*—Sheela Huff
*Assistant Examiner*—Julie E. Reeves
*Attorney, Agent, or Firm*—Howell & Haferkamp, L.C.

[57] ABSTRACT

Novel forms of mutant BAD polypeptides or fragments thereof having an amino acid substitution for serine-112 and/or serine-136 are provided along with their encoding polynucleotides. Also disclosed are methods for preparation of the mutant BAD polypeptides and methods for treating disease conditions involving decreased apoptosis.

18 Claims, 18 Drawing Sheets

Western 10929 α-BAD

Western 12CA5

IP α-BAD
$^{35}$S-labeling

Western
α-14-3-3

$^{32}$P-peptide  Cold Peptide $^{32}$P-peptide  Cold Peptide

| BAD Ser136 | BAD Ser112 | RAF1 Ser259 |
|---|---|---|
| R S X S X P | R S X S X P | R S X S X P |
| R G R S pS A P | R S R H S pS Y P | R Q R S T pS T P |
| R X R X X S | R X R X X S | R X R X X S |

FIGURE 6

α-BAD Western

α-Bad Western $^{32}$p-labeling

α-BAD Western

Western α-14-3-3

Figure 10a

Murine BAD polypeptide (SEQ ID NO:1)

MGTPKQPSLAPAHALGLRKSDPGIRSLGSDAGGRRWRPAAQSMFQIPEFEPSEQEDASATDR
GLGPSLTEDQPGPYLAPGLLGSNIHQQGRAATNSHHGGAGAMETRSRHSSYPAGTEEDEGME
EELSPFRGRSRSAPPNLWAAQRYGRELRRMSDEFEGSFKGLPRPKSAGTATQMRQSAGWTRI
IQSWWDRNLGKGGSTPSQ

Figure 10b

Murine bad polynucleotide (SEQ ID NO:15)

5'-ATGGGAACCCCAAAGCAGCCCTCGCTGGCTCCTGCACACGCCCTAGGCTTGAGGAAGTCC
GATCCCGGAATCCGGAGCCTGGGGAGCGACGCGGGAGGAAGGCGGTGGAGACCAGCAGCCCAG
AGTATGTTCCAGATCCCAGAGTTTGAGCCGAGTGAGCAGGAAGACGCTAGTGCTACAGATAGG
GGCCTGGGCCCTAGCCTCACTGAGGACCAGCCAGGTCCCTACCTGGCCCCAGGTCTCCTGGGG
AGCAACATTCATCAGCAGGGACGGGCAGCCACCAACAGTCATCATGGAGGCGCAGGGGCTATG
GAGACTCGGAGTCGCCACAGTTCGTACCCAGCGGGGACCGAGGAGGATGAAGGGATGGAGGAG
GAGCTTAGCCCTTTTCGAGGACGCTCGCGTTCGGCTCCCCCCAATCTCTGGGCAGCGCAGCGC
TACGGCCGTGAGCTCCGAAGGATGAGCGATGAGTTTGAGGGTTCCTTCAAGGGACTTCCTCGC
CCAAAGAGCGCAGGCACTGCAACACAGATGCGACAAAGCGCCGGCTGGACGCGCATTATCCAG
TCCTGGTGGGATCGAAACTTGGGCAAAGGAGGCTCCACCCCCTCCCAGTGA-3'

FIGURE 11

Human BAD Partial Polynucleotide and Polypeptide Sequences

```
GGCGCTGGGGCTGTGGAGATCCGGAGTCGCCACAGCTCCTACCCCGCGGGACGGAGGAC    60
 G  A  G  A  V  E  I  R  S  R  H  S  S  Y  P  A  G  T  E  D    20
GACGAAGGGATGGGGGAGGAGCCCAGCCCCTTTCGGGGCCGCTCGCGCTCGGCGCCCCC   120
 D  E  G  M  G  E  E  P  S  P  F  R  G  R  S  R  S  A  P  P    40
AACCTCTGGGCCAGCACAGCCGCTATGGCCCGAGCTCCGGAGGATGAGTGACGAGTTTGTG  180
 N  L  W  A  A  Q  R  Y  G  R  E  L  R  R  M  S  D  E  F  V    60
GACTCCTTT                                                       189
 D  S  F                                                         63
```

FIGURE 12

Murine BAD and Partial Human BAD sequences

```
mBAD  MGTPKQPSLAPAHALGLRKSDPGIRSLGSDAGGRRWRPAAQSMFQIPEFE           50 mBAD  PSEQEDASATDRGLGPSLTEDQPGPYLAPGLLGSNIHQQGRAATNSHHGG          100
                                                      —
hBAD                                                  G            1
                                                 *  *
mBAD  AGAMETRSRHSSYPAGTEEDEGMEEELSPFRGRSRSAPPNLWAAQRYGRE          150
      |||•|  ||||||||||||||•||   || ||||||||||||||||||||
hBAD  AGAVEIRSRHSSYPAGTEDDEGMGEEPSPFRGRSRSAPPNLWAAQRYGRE           51 mBAD  LRRMSDEFEGSFKGLPRPKSAGTATQMRQSAGWTRIIQSWWDRNLGKGGS          200
      |||||||  ||
hBAD  LRRMSDEFVDSF                                                 63 mBAD  TPSQ                                                        204
```

BH3

| | | | | | | |
|---|---|---|---|---|---|---|
| Bcl-2 | 97 | L | R | Q | A | G | D | D | F | S | 105 |
| Bax | 63 | L | K | R | I | G | D | E | L | D | 71 |
| Bcl-x | 90 | L | R | E | A | G | D | E | F | E | 98 |
| Bak | 77 | L | A | – | I | G | D | D | I | N | 85 |
| Mcl1 | 213 | L | R | R | V | G | D | G | V | Q | 221 |
| Ced-9 | 116 | M | R | V | M | G | T | I | F | E | 124 |

| | | | | | | |
|---|---|---|---|---|---|---|
| Bik | 61 | L | A | C | I | G | D | E | M | D | 69 |
| Bid | 90 | L | A | Q | I | G | D | E | M | D | 98 |

| | | | | | | | | | |
|---|---|---|---|---|---|---|---|---|---|
| Bcl-2 | 133 | D | G | – | V | N | W | G | R | I | V | A | 142 |
| Bax | 102 | D | G | N | F | N | W | G | R | V | V | A | 112 |
| Bcl-x | 140 | D | G | – | V | N | W | G | R | I | V | A | 149 |
| Bak | 121 | S | G | – | I | N | W | G | R | I | V | A | 130 |
| Mcl1 | 256 | D | G | V | T | N | W | G | R | I | V | T | 266 |
| Ced-9 | 164 | C | P | – | M | S | Y | G | R | L | I | G | 173 |
| A1 | 81 | D | G | I | N | W | G | R | I | V | T | 91 |
| Bad | 142 | W | A | A | Q | R | Y | G | R | E | L | R | 152 |
| LMW5-HL | 80 | D | L | – | I | N | W | G | R | I | C | G | 89 |
| BHRF1 | 93 | R | G | D | P | S | L | G | R | A | L | A | 103 |

|   |   |   |   |   |   |   |   |   |     |
|---|---|---|---|---|---|---|---|---|-----|
| 188 | W | I | Q | D | N | G | G | W | D | 196 |
| 151 | W | I | Q | D | Q | G | G | W | D | 159 |
| 181 | W | I | Q | E | N | G | G | W | D | 189 |
| 170 | W | I | A | Q | R | G | G | W | V | 178 |
| 305 | W | L | V | K | Q | R | G | W | D | 313 |
| 214 | W | K | E | H | N | R | S | W | D | 222 |
| 133 | W | I | R | G | N | G | G | W | E | 141 |
| 183 | W | T | R | I | – | Q | S | W | W | 191 |
| 127 | W | M | I | S | H | G | G | W | E | 135 |
| 143 | W | I | H | Q | Q | G | G | W | D | 151 |

| | | | | | | | | | | | | | | | |
|---|---|---|---|---|---|---|---|---|---|---|---|---|---|---|---|
| Bcl-2 | 11 | N | R | E | . | . | . | . | I | V | M | K | Y | I | H | Y | K | L | S | Q | R | G | Y | E | W | 30 |
| Bcl-x | 5 | N | R | E | . | . | . | . | L | V | V | D | F | L | S | Y | K | L | S | Q | K | G | Y | S | W | 24 |
| Ced-9 | 73 | W | E | E | P | R | L | D | I | E | G | F | V | V | D | Y | F | T | H | R | I | R | Q | N | G | M | E | W | 99 |

Figure 13e

SEQUENCE LISTING ( 1 ) GENERAL INFORMATION:

( i i i ) NUMBER OF SEQUENCES: 60

( 2 ) INFORMATION FOR SEQ ID NO:1:

( i ) SEQUENCE CHARACTERISTICS:
        ( A ) LENGTH: 204 amino acids
        ( B ) TYPE: amino acid
        ( C ) STRANDEDNESS:
        ( D ) TOPOLOGY: linear ( i i ) MOLECULE TYPE: protein ( x i ) SEQUENCE DESCRIPTION: SEQ ID NO:1:

```
Met Gly Thr Pro Lys Gln Pro Ser Leu Ala Pro Ala His Ala Leu Gly
 1               5                  10                  15
Leu Arg Lys Ser Asp Pro Gly Ile Arg Ser Leu Gly Ser Asp Ala Gly
             20                  25                  30
Gly Arg Arg Trp Arg Pro Ala Ala Gln Ser Met Phe Gln Ile Pro Glu
         35                  40                  45
Phe Glu Pro Ser Glu Gln Glu Asp Ala Ser Ala Thr Asp Arg Gly Leu
     50                  55                  60
Gly Pro Ser Leu Thr Glu Asp Gln Pro Gly Pro Tyr Leu Ala Pro Gly
 65                  70                  75                  80
Leu Leu Gly Ser Asn Ile His Gln Gln Gly Arg Ala Ala Thr Asn Ser
                 85                  90                  95
His His Gly Gly Ala Gly Ala Met Glu Thr Arg Ser Arg His Ser Ser
             100                 105                 110
Tyr Pro Ala Gly Thr Glu Glu Asp Glu Gly Met Glu Glu Glu Leu Ser
         115                 120                 125
Pro Phe Arg Gly Arg Ser Arg Ser Ala Pro Pro Asn Leu Trp Ala Ala
     130                 135                 140
Gln Arg Tyr Gly Arg Glu Leu Arg Arg Met Ser Asp Glu Phe Glu Gly
145                 150                 155                 160
Ser Phe Lys Gly Leu Pro Arg Pro Lys Ser Ala Gly Thr Ala Thr Gln
                 165                 170                 175
Met Arg Gln Ser Ala Gly Trp Thr Arg Ile Ile Gln Ser Trp Trp Asp
             180                 185                 190
Arg Asn Leu Gly Lys Gly Gly Ser Thr Pro Ser Gln
         195                 200
```

( 2 ) INFORMATION FOR SEQ ID NO:2:

( i ) SEQUENCE CHARACTERISTICS:
        ( A ) LENGTH: 6 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:2:

```
Arg Ser Xaa Ser Xaa Pro
 1               5
```

( 2 ) INFORMATION FOR SEQ ID NO:3:

( i ) SEQUENCE CHARACTERISTICS:
        ( A ) LENGTH: 6 amino acids (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:3:

Arg  Xaa  Arg  Xaa  Xaa  Ser
     1                 5

(2) INFORMATION FOR SEQ ID NO:4:

(i) SEQUENCE CHARACTERISTICS:
        (A) LENGTH: 6 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:4:

Arg  Ser  Arg  Ser  Ala  Pro
     1                 5

(2) INFORMATION FOR SEQ ID NO:5:

(i) SEQUENCE CHARACTERISTICS:
        (A) LENGTH: 6 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:5:

Arg  Gly  Arg  Ser  Arg  Ser
     1                 5

(2) INFORMATION FOR SEQ ID NO:6:

(i) SEQUENCE CHARACTERISTICS:
        (A) LENGTH: 6 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 4
        (D) OTHER INFORMATION: /note= "PHOSPHORYLATED SERINE"

(xi) SEQUENCE DESCRIPTION: SEQ ID NO:6:

Arg  Ser  Arg  Xaa  Ala  Pro
     1                 5

(2) INFORMATION FOR SEQ ID NO:7:

(i) SEQUENCE CHARACTERISTICS:
        (A) LENGTH: 6 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 6
        (D) OTHER INFORMATION: /note= "PHOSPHORYLATED SERINE"

( x i ) SEQUENCE DESCRIPTION: SEQ ID NO:7:

Arg Gly Arg Ser Arg Xaa
1               5

( 2 ) INFORMATION FOR SEQ ID NO:8:

( i ) SEQUENCE CHARACTERISTICS:
        ( A ) LENGTH: 6 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:8:

Arg His Ser Ser Tyr Pro
1               5

( 2 ) INFORMATION FOR SEQ ID NO:9:

( i ) SEQUENCE CHARACTERISTICS:
        ( A ) LENGTH: 6 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:9:

Arg Ser Arg His Ser Ser
1               5

( 2 ) INFORMATION FOR SEQ ID NO:10:

( i ) SEQUENCE CHARACTERISTICS:
        ( A ) LENGTH: 6 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( A ) NAME/KEY: Modified-site
        ( B ) LOCATION: 4
        ( D ) OTHER INFORMATION: /note= "PHOSPHORYLATED SERINE"

( x i ) SEQUENCE DESCRIPTION: SEQ ID NO:10:

Arg His Ser Xaa Tyr Pro
1               5

( 2 ) INFORMATION FOR SEQ ID NO:11:

( i ) SEQUENCE CHARACTERISTICS:
        ( A ) LENGTH: 6 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( A ) NAME/KEY: Modified-site
        ( B ) LOCATION: 6
        ( D ) OTHER INFORMATION: /note= "PHOSPHORYLATED SERINE"

( x i ) SEQUENCE DESCRIPTION: SEQ ID NO:11:

Arg Ser Arg His Ser Xaa
1               5

(2) INFORMATION FOR SEQ ID NO:12:

(i) SEQUENCE CHARACTERISTICS:
    (A) LENGTH: 204 amino acids
    (B) TYPE: amino acid
    (C) STRANDEDNESS:
    (D) TOPOLOGY: linear (ii) MOLECULE TYPE: peptide (xi) SEQUENCE DESCRIPTION: SEQ ID NO:12:

```
Met Gly Thr Pro Lys Gln Pro Ser Leu Ala Pro Ala His Ala Leu Gly
 1               5                  10                  15

Leu Arg Lys Ser Asp Pro Gly Ile Arg Ser Leu Gly Ser Asp Ala Gly
                20                  25                  30

Gly Arg Arg Trp Arg Pro Ala Ala Gln Ser Met Phe Gln Ile Pro Glu
            35                  40                  45

Phe Glu Pro Ser Glu Gln Glu Asp Ala Ser Ala Thr Asp Arg Gly Leu
        50                  55                  60

Gly Pro Ser Leu Thr Glu Asp Gln Pro Gly Pro Tyr Leu Ala Pro Gly
 65                 70                  75                  80

Leu Leu Gly Ser Asn Ile His Gln Gln Gly Arg Ala Ala Thr Asn Ser
                85                  90                  95

His His Gly Gly Ala Gly Ala Met Glu Thr Arg Ser Arg His Ser Ala
            100                 105                 110

Tyr Pro Ala Gly Thr Glu Glu Asp Glu Gly Met Glu Glu Glu Leu Ser
        115                 120                 125

Pro Phe Arg Gly Arg Ser Arg Ser Ala Pro Pro Asn Leu Trp Ala Ala
    130                 135                 140

Gln Arg Tyr Gly Arg Glu Leu Arg Arg Met Ser Asp Glu Phe Glu Gly
145                 150                 155                 160

Ser Phe Lys Gly Leu Pro Arg Pro Lys Ser Ala Gly Thr Ala Thr Gln
                165                 170                 175

Met Arg Gln Ser Ala Gly Trp Thr Arg Ile Ile Gln Ser Trp Trp Asp
                180                 185                 190

Arg Asn Leu Gly Lys Gly Gly Ser Thr Pro Ser Gln
                195                 200
```

(2) INFORMATION FOR SEQ ID NO:13:

(i) SEQUENCE CHARACTERISTICS:
    (A) LENGTH: 204 amino acids
    (B) TYPE: amino acid
    (C) STRANDEDNESS:
    (D) TOPOLOGY: linear (ii) MOLECULE TYPE: peptide (xi) SEQUENCE DESCRIPTION: SEQ ID NO:13:

```
Met Gly Thr Pro Lys Gln Pro Ser Leu Ala Pro Ala His Ala Leu Gly
 1               5                  10                  15

Leu Arg Lys Ser Asp Pro Gly Ile Arg Ser Leu Gly Ser Asp Ala Gly
                20                  25                  30

Gly Arg Arg Trp Arg Pro Ala Ala Gln Ser Met Phe Gln Ile Pro Glu
            35                  40                  45

Phe Glu Pro Ser Glu Gln Glu Asp Ala Ser Ala Thr Asp Arg Gly Leu
        50                  55                  60

Gly Pro Ser Leu Thr Glu Asp Gln Pro Gly Pro Tyr Leu Ala Pro Gly
 65                 70                  75                  80

Leu Leu Gly Ser Asn Ile His Gln Gln Gly Arg Ala Ala Thr Asn Ser
```

|     |     |     |     | 85  |     |     |     | 90  |     |     |     | 95  |     |     |
| --- | --- | --- | --- | --- | --- | --- | --- | --- | --- | --- | --- | --- | --- | --- |
| His | His | Gly | Gly<br>100 | Ala | Gly | Ala | Met | Glu<br>105 | Thr | Arg | Ser | Arg | His<br>110 | Ser | Ser |
| Tyr | Pro | Ala<br>115 | Gly | Thr | Glu | Glu | Asp<br>120 | Glu | Gly | Met | Glu | Glu<br>125 | Glu | Leu | Ser |
| Pro | Phe<br>130 | Arg | Gly | Arg | Ser | Arg<br>135 | Ala | Ala | Pro | Pro | Asn<br>140 | Leu | Trp | Ala | Ala |
| Gln<br>145 | Arg | Tyr | Gly | Arg | Glu<br>150 | Leu | Arg | Arg | Met | Ser<br>155 | Asp | Glu | Phe | Glu | Gly<br>160 |
| Ser | Phe | Lys | Gly | Leu<br>165 | Pro | Arg | Pro | Lys | Ser<br>170 | Ala | Gly | Thr | Ala | Thr<br>175 | Gln |
| Met | Arg | Gln | Ser<br>180 | Ala | Gly | Trp | Thr | Arg<br>185 | Ile | Ile | Gln | Ser | Trp<br>190 | Trp | Asp |
| Arg | Asn | Leu<br>195 | Gly | Lys | Gly | Gly | Ser<br>200 | Thr | Pro | Ser | Gln |

( 2 ) INFORMATION FOR SEQ ID NO:14:

( i ) SEQUENCE CHARACTERISTICS:
        ( A ) LENGTH: 204 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:14:

| Met<br>1 | Gly | Thr | Pro | Lys<br>5 | Gln | Pro | Ser | Leu | Ala<br>10 | Pro | Ala | His | Ala | Leu<br>15 | Gly |
| --- | --- | --- | --- | --- | --- | --- | --- | --- | --- | --- | --- | --- | --- | --- | --- |
| Leu | Arg | Lys | Ser<br>20 | Asp | Pro | Gly | Ile | Arg<br>25 | Ser | Leu | Gly | Ser | Asp<br>30 | Ala | Gly |
| Gly | Arg | Arg<br>35 | Trp | Arg | Pro | Ala | Ala<br>40 | Gln | Ser | Met | Phe | Gln<br>45 | Ile | Pro | Glu |
| Phe | Glu<br>50 | Pro | Ser | Glu | Gln | Glu<br>55 | Asp | Ala | Ser | Ala | Thr<br>60 | Asp | Arg | Gly | Leu |
| Gly<br>65 | Pro | Ser | Leu | Thr | Glu<br>70 | Asp | Gln | Pro | Gly | Pro<br>75 | Tyr | Leu | Ala | Pro | Gly<br>80 |
| Leu | Leu | Gly | Ser | Asn<br>85 | Ile | His | Gln | Gln | Gly<br>90 | Arg | Ala | Ala | Thr | Asn<br>95 | Ser |
| His | His | Gly | Gly<br>100 | Ala | Gly | Ala | Met | Glu<br>105 | Thr | Arg | Ser | Arg | His<br>110 | Ser | Ala |
| Tyr | Pro | Ala<br>115 | Gly | Thr | Glu | Glu | Asp<br>120 | Glu | Gly | Met | Glu | Glu<br>125 | Glu | Leu | Ser |
| Pro | Phe<br>130 | Arg | Gly | Arg | Ser | Arg<br>135 | Ala | Ala | Pro | Pro | Asn<br>140 | Leu | Trp | Ala | Ala |
| Gln<br>145 | Arg | Tyr | Gly | Arg | Glu<br>150 | Leu | Arg | Arg | Met | Ser<br>155 | Asp | Glu | Phe | Glu | Gly<br>160 |
| Ser | Phe | Lys | Gly | Leu<br>165 | Pro | Arg | Pro | Lys | Ser<br>170 | Ala | Gly | Thr | Ala | Thr<br>175 | Gln |
| Met | Arg | Gln | Ser<br>180 | Ala | Gly | Trp | Thr | Arg<br>185 | Ile | Ile | Gln | Ser | Trp<br>190 | Trp | Asp |
| Arg | Asn | Leu<br>195 | Gly | Lys | Gly | Gly | Ser<br>200 | Thr | Pro | Ser | Gln |

( 2 ) INFORMATION FOR SEQ ID NO:15:

( i ) SEQUENCE CHARACTERISTICS:
        ( A ) LENGTH: 615 base pairs ( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:15:

| ATGGAACCC | CAAAGCAGCC | CTCGCTGGCT | CCTGCACACG | CCCTAGGCTT | GAGGAAGTCC | 60 |
| GATCCCGGAA | TCCGGAGCCT | GGGGAGCGAC | GCGGGAGGAA | GGCGGTGGAG | ACCAGCAGCC | 120 |
| CAGAGTATGT | TCCAGATCCC | AGAGTTTGAG | CCGAGTGAGC | AGGAAGACGC | TAGTGCTACA | 180 |
| GATAGGGGCC | TGGGCCCTAG | CCTCACTGAG | GACCAGCCAG | GTCCCTACCT | GGCCCCAGGT | 240 |
| CTCCTGGGGA | GCAACATTCA | TCAGCAGGGA | CGGGCAGCCA | CCAACAGTCA | TCATGGAGGC | 300 |
| GCAGGGGCTA | TGGAGACTCG | GAGTCGCCAC | AGTTCGTACC | CAGCGGGGAC | CGAGGAGGAT | 360 |
| GAAGGGATGG | AGGAGGAGCT | TAGCCCTTTT | CGAGGACGCT | CGCGTTCGGC | TCCCCCCAAT | 420 |
| CTCTGGGCAG | CGCAGCGCTA | CGGCCGTGAG | CTCCGAAGGA | TGAGCGATGA | GTTTGAGGGT | 480 |
| TCCTTCAAGG | GACTTCCTCG | CCCAAAGAGC | GCAGGCACTG | CAACACAGAT | GCGACAAAGC | 540 |
| GCCGGCTGGA | CGCGCATTAT | CCAGTCCTGG | TGGGATCGAA | ACTTGGGCAA | AGGAGGCTCC | 600 |
| ACCCCCTCCC | AGTGA | | | | | 615 |

( 2 ) INFORMATION FOR SEQ ID NO:16:

( i ) SEQUENCE CHARACTERISTICS:
( A ) LENGTH: 615 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:16:

| ATGGAACCC | CAAAGCAGCC | CTCGCTGGCT | CCTGCACACG | CCCTAGGCTT | GAGGAAGTCC | 60 |
| GATCCCGGAA | TCCGGAGCCT | GGGGAGCGAC | GCGGGAGGAA | GGCGGTGGAG | ACCAGCAGCC | 120 |
| CAGAGTATGT | TCCAGATCCC | AGAGTTTGAG | CCGAGTGAGC | AGGAAGACGC | TAGTGCTACA | 180 |
| GATAGGGGCC | TGGGCCCTAG | CCTCACTGAG | GACCAGCCAG | GTCCCTACCT | GGCCCCAGGT | 240 |
| CTCCTGGGGA | GCAACATTCA | TCAGCAGGGA | CGGGCAGCCA | CCAACAGTCA | TCATGGAGGC | 300 |
| GCAGGGGCTA | TGGAGACTCG | GAGTCGCCAC | AGTGCGTACC | CAGCGGGGAC | CGAGGAGGAT | 360 |
| GAAGGGATGG | AGGAGGAGCT | TAGCCCTTTT | CGAGGACGCT | CGCGTTCGGC | TCCCCCCAAT | 420 |
| CTCTGGGCAG | CGCAGCGCTA | CGGCCGTGAG | CTCCGAAGGA | TGAGCGATGA | GTTTGAGGGT | 480 |
| TCCTTCAAGG | GACTTCCTCG | CCCAAAGAGC | GCAGGCACTG | CAACACAGAT | GCGACAAAGC | 540 |
| GCCGGCTGGA | CGCGCATTAT | CCAGTCCTGG | TGGGATCGAA | ACTTGGGCAA | AGGAGGCTCC | 600 |
| ACCCCCTCCC | AGTGA | | | | | 615 |

( 2 ) INFORMATION FOR SEQ ID NO:17:

( i ) SEQUENCE CHARACTERISTICS:
( A ) LENGTH: 615 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:17:

| ATGGAACCC | CAAAGCAGCC | CTCGCTGGCT | CCTGCACACG | CCCTAGGCTT | GAGGAAGTCC | 60 |

-continued

```
GATCCCGGAA  TCCGGAGCCT  GGGGAGCGAC  GCGGGAGGAA  GGCGGTGGAG  ACCAGCAGCC    120
CAGAGTATGT  TCCAGATCCC  AGAGTTTGAG  CCGAGTGAGC  AGGAAGACGC  TAGTGCTACA    180
GATAGGGGCC  TGGGCCCTAG  CCTCACTGAG  GACCAGCCAG  GTCCCTACCT  GGCCCCAGGT    240
CTCCTGGGGA  GCAACATTCA  TCAGCAGGGA  CGGGCAGCCA  CCAACAGTCA  TCATGGAGGC    300
GCAGGGGCTA  TGGAGACTCG  GAGTCGCCAC  AGTTCGTACC  CAGCGGGGAC  CGAGGAGGAT    360
GAAGGGATGG  AGGAGGAGCT  TAGCCCTTTT  CGAGGACGCT  CGCGTGCGGC  TCCCCCCAAT    420
CTCTGGGCAG  CGCAGCGCTA  CGGCCGTGAG  CTCCGAAGGA  TGAGCGATGA  GTTTGAGGGT    480
TCCTTCAAGG  GACTTCCTCG  CCCAAAGAGC  GCAGGCACTG  CAACACAGAT  GCGACAAAGC    540
GCCGGCTGGA  CGCGCATTAT  CCAGTCCTGG  TGGGATCGAA  ACTTGGGCAA  AGGAGGCTCC    600
ACCCCCTCCC  AGTGA                                                         615
```

( 2 ) INFORMATION FOR SEQ ID NO:18:

( i ) SEQUENCE CHARACTERISTICS:
    ( A ) LENGTH: 615 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:18:

```
ATGGAACCC   CAAAGCAGCC  CTCGCTGGCT  CCTGCACACG  CCCTAGGCTT  GAGGAAGTCC    60
GATCCCGGAA  TCCGGAGCCT  GGGGAGCGAC  GCGGGAGGAA  GGCGGTGGAG  ACCAGCAGCC    120
CAGAGTATGT  TCCAGATCCC  AGAGTTTGAG  CCGAGTGAGC  AGGAAGACGC  TAGTGCTACA    180
GATAGGGGCC  TGGGCCCTAG  CCTCACTGAG  GACCAGCCAG  GTCCCTACCT  GGCCCCAGGT    240
CTCCTGGGGA  GCAACATTCA  TCAGCAGGGA  CGGGCAGCCA  CCAACAGTCA  TCATGGAGGC    300
GCAGGGGCTA  TGGAGACTCG  GAGTCGCCAC  AGTGCGTACC  CAGCGGGGAC  CGAGGAGGAT    360
GAAGGGATGG  AGGAGGAGCT  TAGCCCTTTT  CGAGGACGCT  CGCGTGCGGC  TCCCCCCAAT    420
CTCTGGGCAG  CGCAGCGCTA  CGGCCGTGAG  CTCCGAAGGA  TGAGCGATGA  GTTTGAGGGT    480
TCCTTCAAGG  GACTTCCTCG  CCCAAAGAGC  GCAGGCACTG  CAACACAGAT  GCGACAAAGC    540
GCCGGCTGGA  CGCGCATTAT  CCAGTCCTGG  TGGGATCGAA  ACTTGGGCAA  AGGAGGCTCC    600
ACCCCCTCCC  AGTGA                                                         615
```

( 2 ) INFORMATION FOR SEQ ID NO:19:

( i ) SEQUENCE CHARACTERISTICS:
    ( A ) LENGTH: 9 amino acids
    ( B ) TYPE: amino acid
    ( C ) STRANDEDNESS:
    ( D ) TOPOLOGY: linear ( i i ) MOLECULE TYPE: peptide ( x i ) SEQUENCE DESCRIPTION: SEQ ID NO:19:

```
Leu  Arg  Gln  Ala  Gly  Asp  Asp  Phe  Ser
 1                    5
```

( 2 ) INFORMATION FOR SEQ ID NO:20:

( i ) SEQUENCE CHARACTERISTICS:
    ( A ) LENGTH: 9 amino acids
    ( B ) TYPE: amino acid
    ( C ) STRANDEDNESS:
    ( D ) TOPOLOGY: linear (i) MOLECULE TYPE: peptide (xi) SEQUENCE DESCRIPTION: SEQ ID NO:20:

Leu  Lys  Arg  Ile  Gly  Asp  Glu  Leu  Asp
     1                    5

(2) INFORMATION FOR SEQ ID NO:21:

(i) SEQUENCE CHARACTERISTICS:
        (A) LENGTH: 9 amino acids
        (B) TYPE: amino acid
        (C) STRANDEDNESS:
        (D) TOPOLOGY: linear (i i) MOLECULE TYPE: peptide (xi) SEQUENCE DESCRIPTION: SEQ ID NO:21:

Leu  Arg  Glu  Ala  Gly  Asp  Glu  Phe  Glu
     1                    5

(2) INFORMATION FOR SEQ ID NO:22:

(i) SEQUENCE CHARACTERISTICS:
        (A) LENGTH: 9 amino acids
        (B) TYPE: amino acid
        (C) STRANDEDNESS:
        (D) TOPOLOGY: linear (i i) MOLECULE TYPE: peptide (xi) SEQUENCE DESCRIPTION: SEQ ID NO:22:

Leu  Ala  Ile  Ile  Gly  Asp  Asp  Ile  Asn
     1                    5

(2) INFORMATION FOR SEQ ID NO:23:

(i) SEQUENCE CHARACTERISTICS:
        (A) LENGTH: 9 amino acids
        (B) TYPE: amino acid
        (C) STRANDEDNESS:
        (D) TOPOLOGY: linear (i i) MOLECULE TYPE: peptide (xi) SEQUENCE DESCRIPTION: SEQ ID NO:23:

Leu  Arg  Arg  Val  Gly  Asp  Gly  Val  Gln
     1                    5

(2) INFORMATION FOR SEQ ID NO:24:

(i) SEQUENCE CHARACTERISTICS:
        (A) LENGTH: 9 amino acids
        (B) TYPE: amino acid
        (C) STRANDEDNESS:
        (D) TOPOLOGY: linear (i i) MOLECULE TYPE: peptide (xi) SEQUENCE DESCRIPTION: SEQ ID NO:24:

Met  Arg  Val  Met  Gly  Thr  Ile  Phe  Glu
     1                    5

(2) INFORMATION FOR SEQ ID NO:25:

(i) SEQUENCE CHARACTERISTICS:
        (A) LENGTH: 9 amino acids
        (B) TYPE: amino acid
        (C) STRANDEDNESS:
        (D) TOPOLOGY: linear (  i i  ) MOLECULE TYPE: peptide ( x i ) SEQUENCE DESCRIPTION: SEQ ID NO:25:

Leu Ala Cys Ile Gly Asp Glu Met Asp
1               5

( 2 ) INFORMATION FOR SEQ ID NO:26:

( i ) SEQUENCE CHARACTERISTICS:
    ( A ) LENGTH: 9 amino acids
    ( B ) TYPE: amino acid
    ( C ) STRANDEDNESS:
    ( D ) TOPOLOGY: linear ( i i ) MOLECULE TYPE: peptide ( x i ) SEQUENCE DESCRIPTION: SEQ ID NO:26:

Leu Ala Gln Ile Gly Asp Glu Met Asp
1               5

( 2 ) INFORMATION FOR SEQ ID NO:27:

( i ) SEQUENCE CHARACTERISTICS:
    ( A ) LENGTH: 10 amino acids
    ( B ) TYPE: amino acid
    ( C ) STRANDEDNESS:
    ( D ) TOPOLOGY: linear ( i i ) MOLECULE TYPE: peptide ( x i ) SEQUENCE DESCRIPTION: SEQ ID NO:27:

Asp Gly Val Asn Trp Gly Arg Ile Val Ala
1               5                   1 0

( 2 ) INFORMATION FOR SEQ ID NO:28:

( i ) SEQUENCE CHARACTERISTICS:
    ( A ) LENGTH: 11 amino acids
    ( B ) TYPE: amino acid
    ( C ) STRANDEDNESS:
    ( D ) TOPOLOGY: linear ( i i ) MOLECULE TYPE: peptide ( x i ) SEQUENCE DESCRIPTION: SEQ ID NO:28:

Asp Gly Asn Phe Asn Trp Gly Arg Val Val Ala
1               5                   1 0

( 2 ) INFORMATION FOR SEQ ID NO:29:

( i ) SEQUENCE CHARACTERISTICS:
    ( A ) LENGTH: 10 amino acids
    ( B ) TYPE: amino acid
    ( C ) STRANDEDNESS:
    ( D ) TOPOLOGY: linear ( i i ) MOLECULE TYPE: peptide ( x i ) SEQUENCE DESCRIPTION: SEQ ID NO:29:

Asp Gly Val Asn Trp Gly Arg Ile Val Ala
1               5                   1 0

( 2 ) INFORMATION FOR SEQ ID NO:30:

( i ) SEQUENCE CHARACTERISTICS:
    ( A ) LENGTH: 10 amino acids
    ( B ) TYPE: amino acid
    ( C ) STRANDEDNESS:
    ( D ) TOPOLOGY: linear ( i i ) MOLECULE TYPE: peptide ( x i ) SEQUENCE DESCRIPTION: SEQ ID NO:30:

Ser Gly Ile Asn Trp Gly Arg Val Val Ala
 1               5                   10

( 2 ) INFORMATION FOR SEQ ID NO:31:

( i ) SEQUENCE CHARACTERISTICS:
      ( A ) LENGTH: 11 amino acids
      ( B ) TYPE: amino acid
      ( C ) STRANDEDNESS:
      ( D ) TOPOLOGY: linear ( i i ) MOLECULE TYPE: peptide ( x i ) SEQUENCE DESCRIPTION: SEQ ID NO:31:

Asp Gly Val Thr Asn Trp Gly Arg Ile Val Thr
 1               5                   10

( 2 ) INFORMATION FOR SEQ ID NO:32:

( i ) SEQUENCE CHARACTERISTICS:
      ( A ) LENGTH: 10 amino acids
      ( B ) TYPE: amino acid
      ( C ) STRANDEDNESS:
      ( D ) TOPOLOGY: linear ( i i ) MOLECULE TYPE: peptide ( x i ) SEQUENCE DESCRIPTION: SEQ ID NO:32:

Cys Pro Met Ser Tyr Gly Arg Leu Ile Gly
 1               5                   10

( 2 ) INFORMATION FOR SEQ ID NO:33:

( i ) SEQUENCE CHARACTERISTICS:
      ( A ) LENGTH: 11 amino acids
      ( B ) TYPE: amino acid
      ( C ) STRANDEDNESS:
      ( D ) TOPOLOGY: linear ( i i ) MOLECULE TYPE: peptide ( x i ) SEQUENCE DESCRIPTION: SEQ ID NO:33:

Asp Gly Ile Ile Asn Trp Gly Arg Ile Val Thr
 1               5                   10

( 2 ) INFORMATION FOR SEQ ID NO:34:

( i ) SEQUENCE CHARACTERISTICS:
      ( A ) LENGTH: 11 amino acids
      ( B ) TYPE: amino acid
      ( C ) STRANDEDNESS:
      ( D ) TOPOLOGY: linear ( i i ) MOLECULE TYPE: peptide ( x i ) SEQUENCE DESCRIPTION: SEQ ID NO:34:

Trp Ala Ala Gln Arg Tyr Gly Arg Glu Leu Arg
 1               5                   10

( 2 ) INFORMATION FOR SEQ ID NO:35:

( i ) SEQUENCE CHARACTERISTICS:
      ( A ) LENGTH: 10 amino acids
      ( B ) TYPE: amino acid
      ( C ) STRANDEDNESS:
      ( D ) TOPOLOGY: linear ( i i ) MOLECULE TYPE: peptide ( x i ) SEQUENCE DESCRIPTION: SEQ ID NO:35:

Asp Leu Ile Asn Trp Gly Arg Ile Cys Gly
1               5                   10

( 2 ) INFORMATION FOR SEQ ID NO:36:

( i ) SEQUENCE CHARACTERISTICS:
        ( A ) LENGTH: 11 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:36:

Arg Gly Asp Pro Ser Leu Gly Arg Ala Leu Ala
1               5                   10

( 2 ) INFORMATION FOR SEQ ID NO:37:

( i ) SEQUENCE CHARACTERISTICS:
        ( A ) LENGTH: 9 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:37:

Trp Ile Gln Asp Asn Gly Gly Trp Asp
1               5

( 2 ) INFORMATION FOR SEQ ID NO:38:

( i ) SEQUENCE CHARACTERISTICS:
        ( A ) LENGTH: 9 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:38:

Trp Ile Gln Asp Gln Gly Gly Trp Asp
1               5

( 2 ) INFORMATION FOR SEQ ID NO:39:

( i ) SEQUENCE CHARACTERISTICS:
        ( A ) LENGTH: 9 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:39:

Trp Ile Gln Glu Asn Gly Gly Trp Asp
1               5

( 2 ) INFORMATION FOR SEQ ID NO:40:

( i ) SEQUENCE CHARACTERISTICS:
        ( A ) LENGTH: 9 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:40:

Trp Ile Ala Gln Arg Gly Gly Trp Val
1               5

( 2 ) INFORMATION FOR SEQ ID NO:41:

( i ) SEQUENCE CHARACTERISTICS:
        ( A ) LENGTH: 9 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:41:

Trp Leu Val Lys Gln Arg Gly Trp Asp
1               5

( 2 ) INFORMATION FOR SEQ ID NO:42:

( i ) SEQUENCE CHARACTERISTICS:
        ( A ) LENGTH: 9 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:42:

Trp Lys Glu His Asn Arg Ser Trp Asp
1               5

( 2 ) INFORMATION FOR SEQ ID NO:43:

( i ) SEQUENCE CHARACTERISTICS:
        ( A ) LENGTH: 9 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:43:

Trp Ile Arg Gly Asn Gly Gly Trp Glu
1               5

( 2 ) INFORMATION FOR SEQ ID NO:44:

( i ) SEQUENCE CHARACTERISTICS:
        ( A ) LENGTH: 9 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:44:

Trp Thr Arg Ile Ile Gln Ser Trp Trp
1               5

( 2 ) INFORMATION FOR SEQ ID NO:45:

( i ) SEQUENCE CHARACTERISTICS:
        ( A ) LENGTH: 9 amino acids
        ( B ) TYPE: amino acid
        ( C ) STRANDEDNESS:
        ( D ) TOPOLOGY: linear (i i) MOLECULE TYPE: peptide (x i) SEQUENCE DESCRIPTION: SEQ ID NO:45:

Trp Met Ile Ser His Gly Gly Trp Glu
1               5

(2) INFORMATION FOR SEQ ID NO:46:

(i) SEQUENCE CHARACTERISTICS:
      (A) LENGTH: 9 amino acids
      (B) TYPE: amino acid
      (C) STRANDEDNESS:
      (D) TOPOLOGY: linear (i i) MOLECULE TYPE: peptide (x i) SEQUENCE DESCRIPTION: SEQ ID NO:46:

Trp Ile His Gln Gln Gly Gly Trp Asp
1               5

(2) INFORMATION FOR SEQ ID NO:47:

(i) SEQUENCE CHARACTERISTICS:
      (A) LENGTH: 20 amino acids
      (B) TYPE: amino acid
      (C) STRANDEDNESS:
      (D) TOPOLOGY: linear (i i) MOLECULE TYPE: peptide (x i) SEQUENCE DESCRIPTION: SEQ ID NO:47:

Asn Arg Glu Ile Val Met Lys Tyr Ile His Tyr Lys Leu Ser Gln Arg
1               5                   10                  15
Gly Tyr Glu Trp
            20

(2) INFORMATION FOR SEQ ID NO:48:

(i) SEQUENCE CHARACTERISTICS:
      (A) LENGTH: 20 amino acids
      (B) TYPE: amino acid
      (C) STRANDEDNESS:
      (D) TOPOLOGY: linear (i i) MOLECULE TYPE: peptide (x i) SEQUENCE DESCRIPTION: SEQ ID NO:48:

Asn Arg Glu Leu Val Val Asp Phe Leu Ser Tyr Lys Leu Ser Gln Lys
1               5                   10                  15
Gly Tyr Ser Trp
            20

(2) INFORMATION FOR SEQ ID NO:49:

(i) SEQUENCE CHARACTERISTICS:
      (A) LENGTH: 27 amino acids
      (B) TYPE: amino acid
      (C) STRANDEDNESS:
      (D) TOPOLOGY: linear (i i) MOLECULE TYPE: peptide (x i) SEQUENCE DESCRIPTION: SEQ ID NO:49:

Trp Glu Glu Pro Arg Leu Asp Ile Glu Gly Phe Val Val Asp Tyr Phe
1               5                   10                  15
Thr His Arg Ile Arg Gln Asn Gly Met Glu Trp
            20                  25

( 2 ) INFORMATION FOR SEQ ID NO:50:

( i ) SEQUENCE CHARACTERISTICS:
　　　　( A ) LENGTH: 12 amino acids
　　　　( B ) TYPE: amino acid
　　　　( C ) STRANDEDNESS:
　　　　( D ) TOPOLOGY: linear ( i i ) MOLECULE TYPE: peptide ( x i ) SEQUENCE DESCRIPTION: SEQ ID NO:50:

Tyr Gly Arg Lys Lys Arg Arg Gln Arg Arg Arg Gly
 1               5                  10

( 2 ) INFORMATION FOR SEQ ID NO:51:

( i ) SEQUENCE CHARACTERISTICS:
　　　　( A ) LENGTH: 189 base pairs
　　　　( B ) TYPE: nucleic acid
　　　　( C ) STRANDEDNESS: single
　　　　( D ) TOPOLOGY: linear ( i i ) MOLECULE TYPE: cDNA ( x i ) SEQUENCE DESCRIPTION: SEQ ID NO:51:

| GGCGCTGGGG | CTGTGGAGAT | CCGGAGTCGC | CACAGCTCCT | ACCCCGCGGG | GACGGAGGAC | 60 |
| GACGAAGGGA | TGGGGGAGGA | GCCCAGCCCC | TTTCGGGGCC | GCTCGCGCTC | GGCGCCCCCC | 120 |
| AACCTCTGGG | CAGCACAGCG | CTATGGCCGC | GAGCTCCGGA | GGATGAGTGA | CGAGTTTGTG | 180 |
| GACTCCTTT | | | | | | 189 |

( 2 ) INFORMATION FOR SEQ ID NO:52:

( i ) SEQUENCE CHARACTERISTICS:
　　　　( A ) LENGTH: 189 base pairs
　　　　( B ) TYPE: nucleic acid
　　　　( C ) STRANDEDNESS: single
　　　　( D ) TOPOLOGY: linear ( i i ) MOLECULE TYPE: cDNA ( x i ) SEQUENCE DESCRIPTION: SEQ ID NO:52:

| GGCGCTGGGG | CTGTGGAGAT | CCGGAGTCGC | CACAGCGCCT | ACCCCGCGGG | GACGGAGGAC | 60 |
| GACGAAGGGA | TGGGGGAGGA | GCCCAGCCCC | TTTCGGGGCC | GCTCGCGCTC | GGCGCCCCCC | 120 |
| AACCTCTGGG | CAGCACAGCG | CTATGGCCGC | GAGCTCCGGA | GGATGAGTGA | CGAGTTTGTG | 180 |
| GACTCCTTT | | | | | | 189 |

( 2 ) INFORMATION FOR SEQ ID NO:53:

( i ) SEQUENCE CHARACTERISTICS:
　　　　( A ) LENGTH: 189 base pairs
　　　　( B ) TYPE: nucleic acid
　　　　( C ) STRANDEDNESS: single
　　　　( D ) TOPOLOGY: linear ( i i ) MOLECULE TYPE: cDNA ( x i ) SEQUENCE DESCRIPTION: SEQ ID NO:53:

| GGCGCTGGGG | CTGTGGAGAT | CCGGAGTCGC | CACAGCTCCT | ACCCCGCGGG | GACGGAGGAC | 60 |
| GACGAAGGGA | TGGGGGAGGA | GCCCAGCCCC | TTTCGGGGCC | GCTCGCGCGC | GGCGCCCCCC | 120 |
| AACCTCTGGG | CAGCACAGCG | CTATGGCCGC | GAGCTCCGGA | GGATGAGTGA | CGAGTTTGTG | 180 |
| GACTCCTTT | | | | | | 189 |

( 2 ) INFORMATION FOR SEQ ID NO:54:

( i ) SEQUENCE CHARACTERISTICS:
        ( A ) LENGTH: 189 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:54:

```
GGCGCTGGGG  CTGTGGAGAT  CCGGAGTCGC  CACAGCGCCT  ACCCCGCGGG  GACGGAGGAC      60
GACGAAGGGA  TGGGGGAGGA  GCCCAGCCCC  TTTCGGGGCC  GCTCGCGCGC  GGCGCCCCCC     120
AACCTCTGGG  CAGCACAGCG  CTATGGCCGC  GAGCTCCGGA  GGATGAGTGA  CGAGTTTGTG     180
GACTCCTTT                                                                 189
```

( 2 ) INFORMATION FOR SEQ ID NO:55:

( i ) SEQUENCE CHARACTERISTICS:
        ( A ) LENGTH: 59 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:55:

```
Gly  Ala  Gly  Ala  Val  Glu  Ile  Arg  Ser  Arg  His  Ser  Ser  Tyr  Pro  Ala
 1                    5                        10                       15
Gly  Thr  Glu  Asp  Asp  Gly  Gly  Met  Gly  Glu  Glu  Pro  Ser  Pro  Phe  Arg
               20                       25                       30
Gly  Arg  Ser  Arg  Ser  Ala  Pro  Pro  Asn  Leu  Trp  Ala  Ala  Gln  Arg  Tyr
           35                       40                       45
Gly  Arg  Glu  Leu  Arg  Arg  Met  Ser  Asp  Glu  Phe
       50                       55
```

( 2 ) INFORMATION FOR SEQ ID NO:56:

( i ) SEQUENCE CHARACTERISTICS:
        ( A ) LENGTH: 59 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:56:

```
Gly  Ala  Gly  Ala  Val  Glu  Ile  Arg  Ser  Arg  His  Ser  Ala  Tyr  Pro  Ala
 1                    5                        10                       15
Gly  Thr  Glu  Asp  Asp  Gly  Gly  Met  Gly  Glu  Glu  Pro  Ser  Pro  Phe  Arg
               20                       25                       30
Gly  Arg  Ser  Arg  Ser  Ala  Pro  Pro  Asn  Leu  Trp  Ala  Ala  Gln  Arg  Tyr
           35                       40                       45
Gly  Arg  Glu  Leu  Arg  Arg  Met  Ser  Asp  Glu  Phe
       50                       55
```

( 2 ) INFORMATION FOR SEQ ID NO:57:

( i ) SEQUENCE CHARACTERISTICS:
        ( A ) LENGTH: 59 amino acids
        ( B ) TYPE: amino acid
        ( C ) STRANDEDNESS:
        ( D ) TOPOLOGY: linear ( i i ) MOLECULE TYPE: peptide (x i) SEQUENCE DESCRIPTION: SEQ ID NO:57:

```
Gly Ala Gly Ala Val Glu Ile Arg Ser Arg His Ser Ser Tyr Pro Ala
 1               5                  10                  15
Gly Thr Glu Asp Asp Glu Gly Met Gly Glu Glu Pro Ser Pro Phe Arg
            20                  25                  30
Gly Arg Ser Arg Ala Ala Pro Pro Asn Leu Trp Ala Ala Gln Arg Tyr
            35              40                  45
Gly Arg Glu Leu Arg Arg Met Ser Asp Glu Phe
            50              55
```

(2) INFORMATION FOR SEQ ID NO:58:

(i) SEQUENCE CHARACTERISTICS:
  (A) LENGTH: 59 amino acids
  (B) TYPE: amino acid
  (C) STRANDEDNESS:
  (D) TOPOLOGY: linear (ii) MOLECULE TYPE: peptide (x i) SEQUENCE DESCRIPTION: SEQ ID NO:58:

```
Gly Ala Gly Ala Val Glu Ile Arg Ser Arg His Ser Ala Tyr Pro Ala
 1               5                  10                  15
Gly Thr Glu Asp Asp Glu Gly Met Gly Glu Glu Pro Ser Pro Phe Arg
            20                  25                  30
Gly Arg Ser Arg Ala Ala Pro Pro Asn Leu Trp Ala Ala Gln Arg Tyr
            35              40                  45
Gly Arg Glu Leu Arg Arg Met Ser Asp Glu Phe
            50              55
```

(2) INFORMATION FOR SEQ ID NO:59:

(i) SEQUENCE CHARACTERISTICS:
  (A) LENGTH: 21 base pairs
  (B) TYPE: nucleic acid
  (C) STRANDEDNESS: single
  (D) TOPOLOGY: linear (ii) MOLECULE TYPE: cDNA (x i) SEQUENCE DESCRIPTION: SEQ ID NO:59:

GCGTACCCAG CGGGGACCGA G  21

(2) INFORMATION FOR SEQ ID NO:60:

(i) SEQUENCE CHARACTERISTICS:
  (A) LENGTH: 21 base pairs
  (B) TYPE: nucleic acid
  (C) STRANDEDNESS: single
  (D) TOPOLOGY: linear (ii) MOLECULE TYPE: cDNA (x i) SEQUENCE DESCRIPTION: SEQ ID NO:60:

GCGGCTCCCC CCAATCTCTG G  21

SERINE SUBSTITUTED MUTANTS OF BCL-X$_L$/BCL-2 ASSOCIATED CELL DEATH REGULATOR

REFERENCE TO GOVERNMENT GRANT

This invention was made with government support under Grant Numbers CA50239. The government has certain rights in this invention.

BACKGROUND OF THE INVENTION

(1) Field of the Invention

This invention relates generally to the regulation of apoptosis and to compositions therefor and, more particularly, to serine substituted mutants of BCL-X$_L$/BCL-2 associated cell death regulator.

(2) Description of the Related Art

Programmed cell death, referred to as apoptosis, plays an indispensable role in the development and maintenance of homeostasis within all multicellular organisms (Raff, *Nature* 356:397–400, 1992 which is incorporated by reference). Genetic and molecular analysis from nematodes to humans has indicated that the apoptotic pathway of cellular suicide is highly conserved (Hengartner and Horvitz, *Cell* 76:1107–1114, 1994 which is incorporated by reference). In addition to being essential for normal development and maintenance, apoptosis is important in the defense against viral infection and in preventing the emergence of cancer.

Considerable progress has been made in identifying the molecules that regulate the apoptotic pathway at each level. Of note, both positive and negative regulators, often encoded within the same family of proteins, characterize the extracellular, cell surface and intracellular steps (Oltvai and Korsmeyer 1994 which is incorporated by reference).

One such family of proteins that constitutes an intracellular checkpoint of apoptosis is the BCL-2 family of proteins. The founding member of this family is the apoptosis-inhibiting protein encoded by the BCL-2 protooncogene which was initially isolated from a follicular lymphoma (Bakhshi et al. *Cell* 41:889–906, 1985; Tsujimoto et al, *Science* 229:1390–1393, 1985; Cleary and Sklar, *Proc Natl Acad Sci USA* 82:7439–7443, 1985 which are incorporated by reference). The BCL-2 protein is a 25 kD, integral membrane protein of the mitochondria. This factor extends survival in many different cell types by inhibiting apoptosis elicited by a variety of death-inducing stimuli (Korsmeyer, *Blood* 80:879–886, 1992 which is incorporated by reference).

The family of BCL-2-related proteins has been defined by sequence homology that is largely based upon conserved motifs termed BCL-homology regions. (Yin et al, *Nature* 369:321–323, 1994 which is incorporated by reference). BCL-homology regions 1 and 2 (BH1 and BH2 ) domains have been shown to be important in dimerization and in modulating apoptosis (Yin et al. *Nature* 369:321–20 323, 1994 which is incorporated by reference). A third homology region, BH3, has also been identified as important to dimerization as well as apoptosis (Boyd et al., *Oncogene* 11:1921–1928; Chittenden et al., *Embo J* 14:5589–5596, 1995 which are incorporated by reference) as has been a fourth homology region, BH4, near the amino terminal end of some family members (Farrow and Brown, *Curr Opin Genet Dev* 6:45–49, 1996 which is incorporated by reference).

Members of this family can heterodimerize and, in most cases, homodimerize as well. The ratio of death antagonists (BCL-2, BCL-X$_L$, MCL-1 and A1 ) to agonists (BAX, BAK, BCL-X$_S$ and BAD) determines which homodimers or heterodimers are formed and the balance of these is believed to determine whether a cell will respond to an apoptotic signal (Oltvai and Korsmeyer, *Cell* 79:189–192, 1994 which is incorporated by reference). Thus, dimerization between agonists and antagonists is competitive. For example, the death promoting molecule BAX forms homodimers that favor death whereas BAX will also form heterodimers with BCL-2 or BCL-X$_L$ (Oltvai et al. 1993 which is incorporated by reference) and the formation of these heterodimers results in inhibition of cell death.

BAD (BCL-X$_L$/BCL-2 Associated Cell Death Regulator) is a death agonist (U.S. Pat. No. 5,622,852 which is incorporated in its entirety by reference), which is a very distant BCL2 family member in sequence homology, having only the BH1 and BH2 domains and lacking the BH3, BH4 and transmembrane anchoring domains. BAD apparently exerts its death promoting effects by heterodimerizing with BCL-2 or BCL-X$_L$, death antagonists (Yang et al., 1995). Thus, BAD may function as an inducer of apoptosis by competing for the apoptosis repressors, BCL-2 and BCL-X$_L$.

BAD does not homodimerize, lacks the typical signal/anchor segment suggesting that its free form may reside in the cytosol, has PEST sequences and a much shorter half-life. These parameters suggested BAD could prove to be more proximal at the BCL2 step perhaps linked to signal events. The BAD polypeptide might, therefore, function in a signal transduction role and provide a potential site for modulation of apoptosis.

The 14-3-3 family of proteins of which there are at least seven mammalian isoforms, are highly conserved and ubiquitously expressed. These proteins bind to and regulate a variety of proteins including a number of proteins involved in signal transduction. 14-3-3 binding has been shown to be sequence-specific to a phosphoserine containing motif (Muslin et al. *Cell* 84:889–896, 1996 which is incorporated by reference). This group identified two serine residues (Serine-259 and Serine-621) in Raf-1 each of which lies within a six amino acid motif and phosphorylation of these serines results in 14-3-3 protein binding at each of these two sites. Furthermore, this group identified a number of proteins that contained this motif and postulated that if appropriately phosphorylated, these other proteins might bind 14-3-3. One such protein was BAD and the motif identified surrounds Serine-136 of BAD. Nevertheless, this reference did not report on any tests to determine whether such binding indeed occurs. Furthermore, the physiologic role of any possible binding of a Serine-136 phosphorylated BAD to 14-3-3 was not considered by this group with only the general suggestion that 14-3-3 might interact with proteins to perform an essential chaperone function. Moreover, this group did not suggest any possible phosphorylation of any other of the Serine residues of BAD such as Serine-112.

Some disease conditions are believed to be related to the development of a defective down-regulation of apoptosis in the affected cells. For example, neoplasias may result, at least in part, from an apoptosis-resistant state in which cell proliferation signals inappropriately exceed cell death signals. Furthermore, some DNA viruses such as Epstein-Barr virus, African swine fever virus and adenovirus, parasitize the host cellular machinery to drive their own replication and at the same time modulate apoptosis to repress cell death and allow the target cell to reproduce the virus. Moreover, certain other disease conditions such as lymphoproliferative conditions, cancer including drug resistant cancer, arthritis, inflammation, autoimmune diseases and the like may result from a down regulation of cell death regulation. In such disease conditions it would be desirable to promote apoptotic mechanisms and one advantageous approach might involve treatment with a cell to modulate the effect of BAD to increase its binding to BCL-2 and/or BCL-$X_L$ and thereby diminish the expression of the death repressor activity of these death antagonists.

Conversely, in certain disease conditions it would be desirable to inhibit apoptosis such as in the treatment of immunodeficiency diseases, including AIDS, senescence, neurodegenerative disease, ischemic and reperfusion cell death, infertility, wound-healing, and the like. In the treatment of such diseases it would be desirable to modulate the effect of BAD to decrease its binding to BCL-2 and/or BCL-$X_L$ and thereby increase the death repressor activity of these death antagonists. Thus, it would be desirable identify new approaches that can alter the binding of BAD to BCL-2 family members and to utilize these as a basis for treatment modalities in advantageously modulating the apoptotic process in disease conditions involving either inappropriate repression or inappropriate acceleration of cell death.

SUMMARY OF THE INVENTION

Accordingly, the inventor herein has succeeded in discovering a new post-translational modification of the BAD polypeptide in which specific serine residues are phosphorylated. The phosphorylated serines are at positions 112 and 136 and the BAD polypeptide can be phosphorylated at one or both of these serine residues. Whereas non-phosphorylated BAD polypeptide heterodimerizes with BCL-2 or BCL-$X_L$ at membrane sites, the phosphorylated BAD polypeptides does not, but instead binds to 14-3-3 within the cytosol. The net result of this phosphorylation of the BAD polypeptide is the promotion of cell survival.

The present invention is based upon the surprising discovery that mutants of the BAD polypeptide having amino acid substitutions at the serine 112 and/or 136 positions are able to bind to BCL-$X_L$, but unable to bind to 14-3-3. These mutants exhibit enhanced death promoting activity compared to the serine-containing BAD polypeptide.

Thus, in one embodiment of the present invention, mutant BAD polypeptides and fragments thereof are provided. The polypeptides are preferably in isolated and substantially purified form. The mutant BAD polypeptides of the present invention are derived from naturally occurring sequences which are believed to have at least about 85% sequence identity among orthologs from different mammalian species and preferably at least about 90% sequence identity compared to the murine sequence. These mutant polypeptides have the same or different amino acid substitutions at positions corresponding to the aligned positions of serine 112 and/or serine 136 of murine BAD as set forth in SEQ ID NO:1. The mutant BAD polypeptides can be characterized in that they (a) lack the carboxyl terminal signal-anchor sequence characteristic of the membrane bound members of the BCL-2 family, (b) lack BH3 and BH4 domains, (c) have a BH1 and BH2 domain and (d) have any amino acid other than Serine independently at position 112 and/or position 136. As used herein, the terms "position 112 and/or position 136" refers to said positions in a BAD polypeptide or mutant BAD polypeptide which are identified by alignment to a murine BAD polypeptide as set forth in SEQ ID NO:1 and which correspond to the serines in said positions in SEQ ID NO:1.

In one aspect of the present invention the mutant BAD polypeptides are capable of binding to BCL-$X_L$, but not to 14-3-3. These mutant BAD polypeptides show an increased ability to promote cell death compared to the non-substituted BAD polypeptides. In one embodiment, the mutant BAD polypeptides can have the amino acid sequences of BH1 and/or a BH2 (FIGS. 13C and 13D). In preferred embodiments, the mutant peptides are comprised of sequences having an alanine residue instead of serine at position 112 (SEQ ID NO:12) or an alanine residue instead of serine at position 136 (SEQ ID NO:13) or alanine residues in both positions 112 and 136 (SEQ ID NO:14). More preferred is the corresponding human BAD polypeptide which can be identified by the partial human BAD sequence (SEQ ID NO:55) and which have alanine substitutions for serine-112 or serine-136 or both (SEQ ID NO:56 or SEQ ID NO:57 or SEQ ID NO:58) or a substantially identical mutein, fragment, analog, or fusion protein of the murine or partial human mutant BAD polypeptide. The mutein, fragment, analog or fusion protein of the serine-112 and/or serine-136 mutant BAD polypeptide are characterized in that they exhibit apoptotic activity to decrease cell viability.

The present invention also provides methods for making a polypeptide having increased death promoting activity. The method comprises preparing a mutant BAD polypeptide wherein the mutant BAD polypeptide can have a BH1 and/or a BH2 domain. The mutant BAD polypeptides have an amino acid other than serine at position 112 and/or position 136 said positions being identified by alignment to a murine BAD polypeptide as set forth in SEQ ID NO:1 or a substantially identical mutein, fragment, analog, or fusion protein derived from said mutant BAD polypeptide.

In another embodiment, polynucleotides are provided which encode mutant BAD polypeptides having the same or different amino acids in the 112 or 136 or both positions. In one preferred embodiment, the polynucleotide encodes a murine bad polypeptide having alanine residues at positions 112 or 136 or both 112 and 136 (SEQ ID NO:16 or SEQ ID NO:17 or SEQ ID NO:18, respectively). In another preferred embodiment, the polynucleotide encodes a partial human bad polypeptide having alanine residues at positions 112 or 136 or both 112 and 136 (SEQ ID NO:52 or SEQ ID NO:53 or SEQ ID NO:54). Such polynucleotides can serve as templates for the recombinant expression of quantities of the mutant BAD polypeptides.

The present invention also provides vectors comprising a recombinant DNA molecule which encodes a mutant BAD polypeptide.

In another embodiment, the present invention provides methods for treating conditions in which cell death is inappropriately inhibited, such as in cancer, viral infections, lymphoproliferative conditions, arthritis, infertility, inflammation, autoimmune diseases and the like. The methods involve administration of a mutant BAD polypeptide or substantially identical mutein, fragment, analog, or fusion protein thereof.

In yet another embodiment, the present invention provides additional methods for treating conditions involving inappropriately inhibited cell death, the methods comprising the administration of a polynucleotide encoding mutant BAD polypeptides or a vector containing the polynucleotide.

In another embodiment, the present invention is comprised of an isolated and substantially purified serine-phosphorylated BAD polypeptide which (a) lacks the carboxyl terminal signal-anchor sequence characteristic of the membrane bound members of the BCL-2 family, (b) lacks BH3 and BH4 domains, (c) has a BH1 and BH2 domain, (d)

has a phosphorylated Serine 112 and/or a phosphorylated Serine 136 and (e) binds to a 14-3-3 protein. The phosphorylated BAD polypeptide can be comprised of a murine BAD sequence, SEQ ID NO:1, which is phosphorylated at the serine-112 position, at the serine-136 position or at both the serine-112 and the serine-136 positions. The phosphorylated BAD polypeptide can also be comprised of a partial human BAD sequence, SEQ ID NO:55, which is phosphorylated at the serine-112 position, at the serine-136 position or at both the serine-112 and the serine-136 positions. These phosphoserine BAD polypeptides can be used in screening assays for inhibitors or activators of serine-phosphatase agents in which a test agent converts the serine-phosphorylated BAD polypeptide to the non-phosphorylated BAD death agonist. The serine-phosphatase inhibitors are believed to be useful in the treatment or prevention of disease states in cells in which apoptosis is inappropriately increased such as immunodeficiency diseases including AIDS, senescence, neurodegenerative disease, ischemic cell death, reperfusion cell death, infertility and wound-healing. Serine-phosphatase activating agents, conversely, can be used to treat diseases in cells in which apoptosis is inappropriately decreased such as cancer, hyperplasias such as benign prostatic hyperplasia, viral infections, lymphoproliferative conditions, arthritis, inflammation and autoimmune diseases.

Fragments of the serine phosphorylated BAD polypeptides are also within the scope of the present invention wherein the fragments contain a phosphorylated serine 112 and/or a phosphorylated serine 136. Such fragments exhibit the same biological activity of the full length sequences although not necessarily to the same degree.

In another embodiment a method for promoting the survival of a cell is provided. The method is comprised of administering to the cell an effective amount of an inhibitor of phosphoserine phosphatase activity on a phosphorylated BAD protein.

The present invention also provides in another embodiment a method for inhibiting survival in a cell with inappropriately decreased apoptotsis. The method comprises administering to the cell an effective amount of an activator of phosphoserine phosphatase activity on a phosphorylated BAD protein.

Another embodiment provides a method for preventing or treating a decreased apoptosis in a cell comprising administering to the cell a serine kinase inhibitor in an amount effective in inhibiting the phosphorylation and binding of a BAD polypeptide to a 14-3-3 protein. One such kinase inhibitor is staurosporin.

Another embodiment provides for a method for preventing or treating an increased apoptosis in a cell comprising administering to the cell a serine kinase activator in an amount effective in increasing the phosphorylation and binding of a BAD polypeptide to a 14-3-3 protein. One such kinase activator is PMA (4-phorbol-12-myristate-12-acetate, a kinase activating phorbol ester).

The present invention also provides a method for identifying an agent which modulates the phosphorylation of a BAD polypeptide. The method is comprised of administering a test agent to a cell line which expresses a BAD polypeptide and a 14-3-3 protein and detecting a change in the phosphorylation of a BAD polypeptide compared to a pretreatment value.

In another embodiment, the present invention provides a method for assessing the apoptotic state of a cell comprising detecting the amounts of phosphorylated and unphosphorylated BAD protein in the cell. In one such embodiment, the method comprises determining the amount of phosphorylated BAD polypeptide by measuring the amount of BAD polypeptide bound to 14-3-3 polypeptide using both anti-BAD and anti-14-3-3 antibodies and determining the amount of unphosphorylated BAD as the difference between total BAD polypeptide, measured with anti-BAD antibody, and the amount of phosphorylated BAD, measured as above.

Among the several advantages found to be achieved by the present invention, therefore, may be noted the provision of new mutant BAD polypeptides and polynucleotides encoding such polypeptides which can promote cell death in cells with inappropriately inhibited cell death such as in neoplasia or autoimmunity, the provision of methods for making such mutant polypeptides and polynucleotides and the provision of methods of treating or preventing such inappropriate inhibition of cell death; the provision of new serine phosphorylated BAD polypeptides as well as fragments thereof which can be used in assay systems to identify new apoptosis modulating agents which are inhibitors or activators of phosphoserine phosphatases; the provision of methods of treating or preventing inappropriate increase or decrease in apoptosis in a cell using phosphoserine phosphatase inhibitors or activators; the provision of methods of treating or preventing inappropriate increase or decrease in apoptosis in a cell using serine kinase inhibitors or activators; the provision of a method for identifying agents which are capable of modulating the phosphorylation of a BAD polypeptide in a cell; and the provision of a method for assessing the apoptotic state of a cell by determining the amounts of phosphorylated and unphosphorylated BAD polypeptide present.

BRIEF DESCRIPTION OF THE DRAWINGS

FIG. 3 illustrates (FIG. 3A) the 2D-map of $^{32}$P-labeled tryptic peptides from in vivo $^{32}$P-phosphorylated, anti-BAD immunoprecipitated BAD.

FIG. 6 illustrates a comparison of consensus 14-3-3 binding motifs surrounding a serine phosphorylation site in RAF1 with serine phosphorylation sites in BAD;

FIG. 10 illustrates (FIG. 10A) the murine BAD polypeptide sequence (SEQ ID NO:1) and (FIG. 10B) the bad polynucleotide sequence encoding the polypeptide (SEQ ID NO:15);

FIG. 11 illustrates the polynucleotide sequence (SEQ ID NO:51) and encoded polypeptide sequence (SEQ ID NO:55) for the partial human BAD polypeptide;

FIG. 12 illustrates the murine BAD polypeptide sequence (SEQ ID NO:1) and the aligned partial human BAD polypeptide sequence (SEQ ID NO:55) with identical amino acid residues identified with vertical lines, conserved residues identified by dots, serine-112 position indicated by single star, serine-136 position indicated by double star, BH1 region indicated by single overline and BH2 region indicated by double overline.

DESCRIPTION OF THE PREFERRED EMBODIMENTS

Figure 1A:
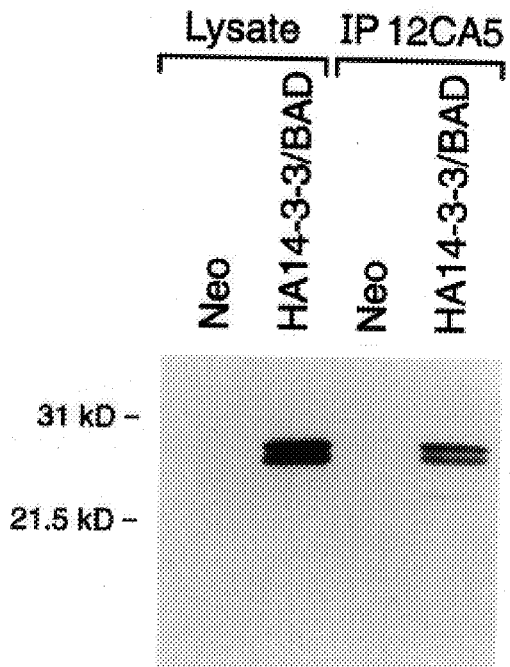
FIG. 1 illustrates (FIG. 1A) an anti-BAD western blot of whole cell lysates and anti-hemagglutinin immunoprecipitated proteins from FL5.12 cells coexpressing HA14-3-3 and BAD, (FIG. 1B) an anti-hemagglutinin western blot of anti-BAD immunoprecipitated proteins from FL5.12 cells coexpressing HA14-3-3 and BAD, (FIG. 1C) an autoradiograph of anti-BAD immunoprecipitated proteins from $^{35}$S-methionine labeled FL5.12 cells coexpressing HA14-3-3 and BAD, and (FIG. 1D) an anti-14-3-3 Western blot of a whole cell lysate and anti-BAD immunoprecipitated proteins from FL5.12 cells coexpressing HA14-3-3 and BAD.
Figure 1B:
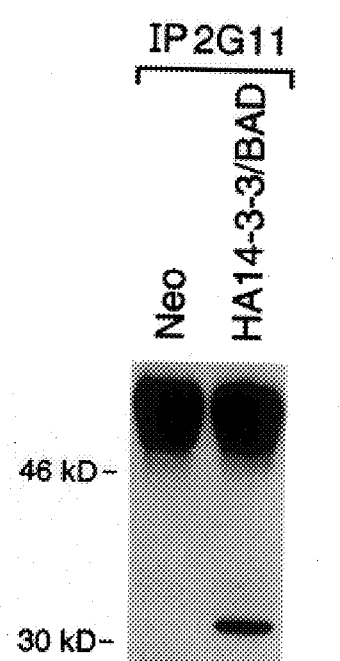
Figure 1C:
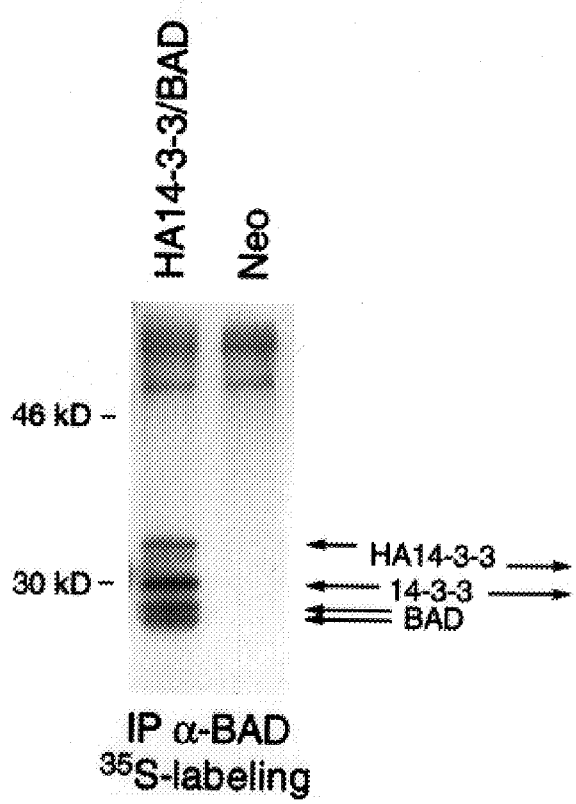
Figure 1D:
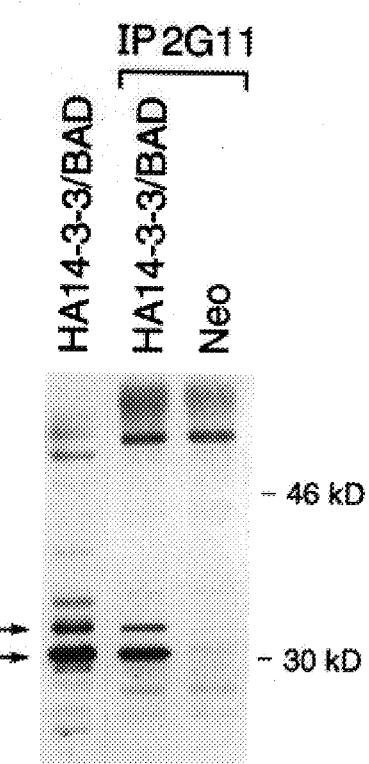

The present invention is based upon the discovery of serine phosphorylated forms of the death agonist BAD. Surprisingly, phosphorylation at either or both of serine-112 and serine-136 residues of BAD results in the BAD polypeptide binding to 14-3-3 protein, but not to BCL-X$_L$. As a result cell death is avoided. While not wishing to be bound to any mechanism of action, this cell death resistance may be due to the sequestering of the phosphorylated BAD polypeptide due to its binding to 14-3-3 polypeptide with the result that the BAD polypeptide is no longer available to bind to BCL-X$_L$ and induce cell death. Alternatively, the BAD polypeptide may itself act as a death agonist when not bound to BCL-X$_L$ or 14-3-3 and the phosphorylation and binding of BAD to 14-3-3 would have the effect of inactivating BAD.

A particularly significant aspect of the present invention is based upon the discovery that substitution of one or both of the serines involved in phosphorylation and binding to 14-3-3 results in a mutant BAD polypeptide that exerts a more potent apoptotic effect than that of the native BAD polypeptide.

The interaction of murine BAD and 14-3-3 protein was discovered using protein interactive expression cloning (Blanar and Rutter, *Science* 256:1014–1018, 1992 which is incorporated by reference). GST-BAD fusion protein bearing a heart muscle kinase (HMK) motif was labeled with [γ-$^{32}$P] ATP in vitro to screen an oligo (dT)-primed mouse embryonic day 16 EXlox cDNA expression library. Two independent clones of the tau form (τ) of 14-3-3 (Nielsen, *Biochem Biophys* 1088:425–428, 1991 which is incorporated by reference) were isolated.

In the presence of survival factor, IL-3, cells phosphorylated the BAD polypeptide on two serine residues that bound to the 14-3-3 polypeptide. Immunoprecipitation and Western blot analysis of the serine phosphorylated BAD polypeptide bound to the 14-3-3 protein revealed a lower band of hypophosphorylated BAD/14-3-3 with either serine-112 or serine-136 phosphorylation on BAD and an upper band of hyperphosphorylated BAD/14-3-3 with both sites phosphorylated.

Phosphorylated BAD resides in the cytosol where it is bound to 14-3-3. Both the double phosphorylated Ser112 and Ser136 BAD of the upper band and single site phosphorylated BAD of the lower band are complexed with 14-3-3. 14-3-3 has been shown to be a motif specific phosphoserine binding protein. Both Serine-112 and Serine-136 of BAD are homologous to the consensus binding motifs for 14-3-3 defined most critically for RAF1 (Muslin et al., 1996 which is incorporated by reference) (FIG. 6A). Serine-136 of BAD possesses both the RSXSXP (SEQ ID NO:2) and overlapping RXRXXS (SEQ ID NO:3) motifs found in RAF1 at its 14-3-3 interaction site (specific sequences for the serine-136 site are, respectively, RSRSAP (SEQ ID NO:4) and RGRSRS (SEQ ID NO:5) in the non-phosphorylated forms and RSR($_p$S)AP (SEQ ID NO:6) and RGRSR($_p$S) (SEQ ID NO:7) in the phosphorylated forms); whereas, Serine-112 only varies at the −2 position (RHSSYP) of the RSXSXP motif (specific sequences for the serine-112 site are, respectively, RHSSYP (SEQ ID NO:8) and RSRHSS (SEQ ID NO:9) in the non-phosphorylated form and RHS($_p$S)YP (SEQ ID NO:10) and RSRHS($_p$S) (SEQ ID NO:11) in the phosphorylated form). The histidine for serine substitution is also present in tyrosine hydroxylase (Furukawa et al., 1993 which is incorporated by reference), a known 14-3-3 binding protein. Thus, either phosphorylated site in BAD appears to be capable of mediating binding with 14-3-3. Moreover, it appears that multiple 14-3-3 isoforms will bind BAD, consistent with the fact that phosphorylated RAF1 peptides showed no 14-3-3 isoform specificity. BAD lends further support to the role of these phosphorylated serine motifs as distinct recognition sites for 14-3-3.

BAD has been shown to have both cytosolic and membrane associated forms consistent with its lack of a COOH-terminal signal/anchor segment found in most BCL-2 family members. This suggested that BAD might be involved in communicating transduced signals from the cytosol to the membrane bound BCL-$X_L$ complex. The phosphorylation of BAD following exposure to IL-3, provides a clear link between an extracellular survival factor and altered susceptibility to apoptosis due to a post-translational modification of the BAD. BAD is rapidly phosphorylated within ten minutes of IL-3 exposure. The phosphorylation of BAD results in its binding to 14-3-3 in the cytosol and precludes its binding to membrane based BCL-$X_L$, an event that enhances survival and provides a new site for regulation of transduced survival signals. The most likely role for 14-3-3 protein is as a chaperone or protective binding protein for BAD that keeps it sequestered in the cytosol. 14-3-3 interaction with phosphorylated BAD might facilitate its translocation from membrane to cytosolic compartments.

Figure 13A:
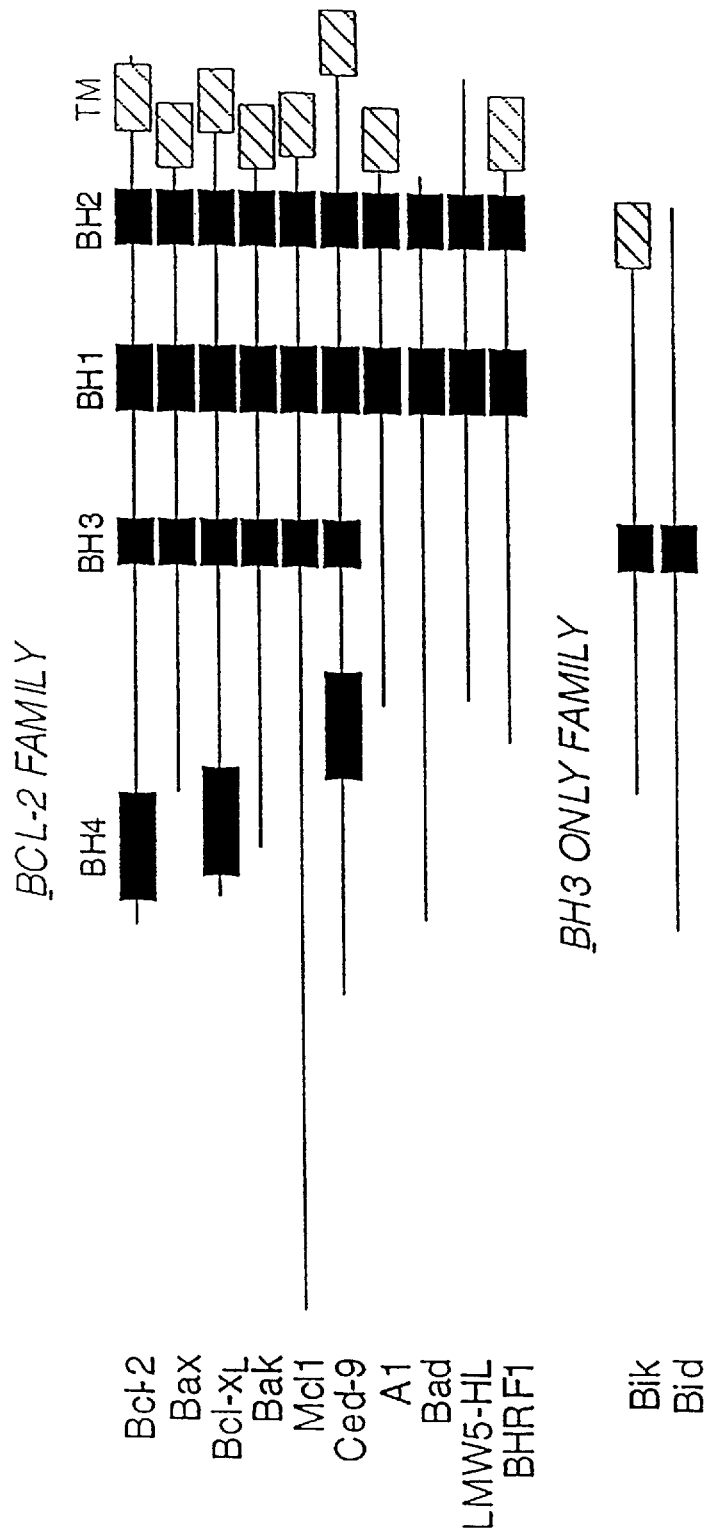
FIG. 13 illustrates (FIG. 13A) the BH1 , BH2 , BH3, BH4 and transmembrane domains of BCL-2 family members and comparison of the sequences of (FIG. 13B) BH3 (SEQ ID NOS: 19–26), (FIG. 13C) BH1 (SEQ ID NOS:27–36), (FIG. 13D) BH2 (SEQ ID NOS:37–46) and (FIG. 13E) BH4 domains (SEQ ID NOS:47–49).

Murine BAD has been sequenced and identified as having BH1 and BH2 domains but lacking BH3, BH4 and signal anchoring domains of the other BCL-2 family members (see U.S. patent application Ser. No. 08/333,565, now U.S. Pat. No. 5,622,852). BH1 and BH2 domains have been identified for a number of the BCL-2 family members including BAD as shown in FIGS. 13C and 13D. A BLAST search revealed two EST sequences from adult human blood which were used to deduce the partial human BAD polypeptide sequence (Accession Nos. Z57098 and Z57099 and sequences therein; *Nature Genet* 6:236–244, 1994 which are incorporated by reference). The polynucleotide sequence and deduced amino acid sequence of the partial human BAD are shown in FIG. 11. Alignment of the partial human BAD polypeptide with the murine BAD polypeptide revealed that the partial human BAD sequence contains a BH1 region and serine residues corresponding to the serine-112 and serine-136 residues of murine BAD (FIG. 12). However, the partial human BAD sequence does not include the portion of the full length human BAD sequence corresponding to the BH2 region of murine BAD. The partial human BAD sequence showed 89% sequence identity and 92% sequence conservation with the corresponding portion of murine BAD. It is believed that inasmuch as the partial human polypeptide contains both serine-112 and serine 136 residues as well as the BH1 domain that this polypeptide will bind to 14-3-3 protein upon phosphorylation of one or both of these serines and that mutant forms of this polypeptide containing an amino acid other than serine at the 112 and/or 136 positions will exert an apoptotic effect greater than that for the partial sequence of the naturally occurring human BAD polypeptide.

The terms "BAD" or "BAD polypeptide" or "BAD protein" as referenced herein includes polypeptide cell death agonists of any origin which are substantially homologous to and which are biologically equivalent to the BAD polypeptides which bind to BCL-2 or BCL-$X_L$ in competition with the death agonists BAX and BAK to inhibit the death repressor activity of BCL-2 or BCL-$X_L$. Reference to mutant BAD or mutant BAD polypeptide or mutant BAD protein is intended to mean the polypeptide cell death agonists in which one or both serine moities corresponding to Serine 112 or Serine 136 of murine BAD have been replaced with an amino acid other than serine identified by alignment of the sequence with murine BAD.

In addition, the present invention is also directed to fragments of a mutant BAD polypeptide containing an amino acid other than serine in one or both positions corresponding to position 112 or position 136 of murine BAD identified by alignment to murine BAD. The fragments contain at least 10 amino acids, more preferably at least 25 amino acids and can approach the number of amino acids in the full length BAD polypeptide. Such fragments are characterized in that they show apoptotic activity to decrease cell viability.

Also within the scope of the present invention are fragments of a BAD polypeptide containing a conserved motif having a serine which upon phosphorylation will bind to 14-3-3 protein. Thus, the BAD polypeptide or fragment thereof, upon phosphorylation at serine residue 112 and/or serine residue 136 or equivalent thereof, binds to 14-3-3 protein but not to BCL-$X_L$.

BAD polypeptides from which mutant BAD polypeptides are derived and serine phosphorylated BAD polypeptides and fragments thereof may be native to any tissue or species and, similarly, biological activity can be characterized in any of a number of biological assay systems.

The terms "biologically equivalent" are intended to mean that the compositions of the present invention are capable of demonstrating some or all of the same apoptosis inducing effects although not necessarily to the same degree as the BAD polypeptide deduced from sequences identified from cDNA libraries of mouse or human origin or produced from recombinant expression systems. The apoptotic activity of a substance can be determined using a number of experimental models and a particularly useful approach is to monitor the percent viability of cells in the presence of the substance. The mutant forms of BAD can show an increased or a decreased apoptotic activity compared to the BAD polypeptide from which the mutant form was derived depending upon the particular mutant. The mutant BAD polypeptides having alanine substitutions for either of the serine 112 or serine 136 moities show an increased apoptotic effect compared to the naturally occurring BAD polypeptide and mutants having both alanine substitutions show a still greater apoptotic effect.

Reference to mutant BAD polypeptides herein preferably includes a mutant BAD polypeptide which has at least 85 percent conservation with any one of SEQ ID NOS:12–14 or SEQ ID NOS:56–58 polypeptides or a mutant bad polynucleotide encoding one such mutant BAD polypeptide (SEQ ID NOS:16–18 or SEQ ID NOS:52–54); more preferably, a mutant BAD polypeptide which has at least 85 percent substantial identity to any one of SEQ ID NOS:12–14 or SEQ ID NOS:55–57 polypeptides or a mutant bad polynucleotide encoding one such mutant BAD polypeptide (SEQ ID NOS:16–18 or SEQ ID NOS:52–54); even more preferably a mutant BAD polypeptide which has at least 90–95 percent conservation with any one of SEQ ID NOS:12–14 or SEQ ID NOS:56–58 polypeptides or a mutant bad polynucleotide encoding one such mutant BAD polypeptide (SEQ ID NOS:16–18 or SEQ ID NOS:52–54); still more preferably, a mutant BAD polypeptide which has at least 90–95 percent substantial identity to any one of SEQ ID NOS:12–14 or SEQ ID NOS:56–58 polypeptides or a mutant bad polynucleotide encoding one such mutant BAD polypeptide (SEQ ID NOS:16–18 or SEQ ID NOS:52–54); even still more preferably, a mutant BAD polypeptide which has 100 percent conservation with any one of SEQ ID NOS:12–14 or SEQ ID NOS:56–58 polypeptides or a mutant bad polynucleotide encoding one such mutant BAD polypeptide (SEQ ID NOS:16–18 or SEQ ID NOS:52–54); and most preferably, a mutant BAD polypeptide which has 100 percent substantial identity to any one of SEQ ID NOS: 12–14 polypeptides or a mutant bad polynucleotide encoding one such mutant BAD polypeptide (SEQ ID NOS: 16–18). Preferred mutant bad polynucleotides are capable of hybridizing with a naturally-occurring bad polynucleotide as set forth in SEQ ID NO:15 or SEQ ID NO:51 under stringency conditions as set forth in Sambrook et al. (Sambrook et al., *Molecular Cloning, 2nd Ed.*, Cold Spring Harbor Laboratory Press, 1989 which is incorporated by reference). In contrast, such mutants do not hybridize to polynucleotides encoding any of the other family members, in particular the bcl-2 polynucleotide, under the same stringency conditions. Such selective hybridization can be shown in typical cross-hybridization tests.

By "substantially homologous" it is meant that the degree of homology of murine BAD polypeptide to a human BAD polypeptide or to a BAD polypeptide from any species is greater than that between BAD and any previously reported member of the BCL-2 family of proteins.

Sequence identity or percent identity is intended to mean the percentage of same residues between two sequences (Higgins et al, *Cabios* 8:189–191, 1992 which is incorporated by reference) of multiple sequence alignment in the Lasergene biocomputing software (DNASTAR, INC, Madison, Wis.). The residue weight table used for the alignment program is PAM250 (Dayhoff et al., in *Atlas of Protein Sequence and Structure, Dayhoff*, Ed., NBRF, Washington, Vol. 5, suppl. 3, p. 345, 1978 which is incorporated by reference). Such alignment allows identification of BH1 and BH2 homology regions and, in particular, it allows identification of serine moieties corresponding to serine 112 and serine 136 of murine BAD polypeptide.

Percent conservation is calculated from the above alignment by adding the percentage of identical residues to the percentage of positions at which the two residues represent a conservative substitution (defined as having a log odds value of greater than or equal to 0.3 in the PAM250 residue weight table). Conservative amino acid changes satisfying this requirement are: R-K; E-D, Y-F, L-M; V-I, Q-H.

BAD polypeptides, serine-substituted mutant BAD polypeptides as well as serine-phosphorylated BAD polypeptides and mutant BAD polypeptides having one serine substitution and one serine phosphorylation can also include derivatives and mutant forms of such polypeptides which also includes hybrid and modified forms of such polypeptides, including fusion proteins and fragments and hybrid and modified forms in which certain amino acids have been deleted or replaced and modifications such as where one or more amino acids have been changed to a modified amino acid or unusual amino acid and modifications such as glycosolations so long as the hybrid or modified form retains the biological activity of BAD. By retaining the biological activity, it is meant that cell death is accelerated by the BAD polypeptide or mutant BAD polypeptide, although not necessarily at the same level of potency as that of the naturally-occurring BAD polypeptide and that can be produced, for example, recombinantly. The level of potentence can be either greater or lesser than the naturally-occurring BAD polypeptide depending upon the particular BAD polypeptide or mutant BAD polypeptide.

Furthermore, in the case of BAD polypeptides and mutant BAD polypeptides having only one serine substitution, such cell death induction is blocked by phosphorylation of serine-112 and/or serine-136 or equivalents thereof.

Also included within the meaning of substantially homologous is any BAD polypeptide which may be isolated by virtue of cross-reactivity with antibodies to the BAD polypeptide described herein. By cross-reaction it is meant that an antibody reacts with an antigen other than the one that induced its formation. Such Bad polypeptides can then have substituted serine residues and/or phosphorylated serine residues. Also included are BAD polypeptides whose encoding nucleotide sequences including genomic DNA, mRNA or cDNA may be isolated through hybridization with the complementary sequence of genomic or subgenomic nucleotide sequences or cDNA of the BAD polynucleotides herein or fragments thereof. Such BAD polypeptides can also have substituted serine residues and/or phosphorylated serine residues. It will also be appreciated by one skilled in the art that degenerate DNA sequences can encode BAD polynucleotide sequences having serine substitutions or having serines which can be phosphorylated and these are also intended to be included within the present invention as are allelic variants of BAD and serine substituted and/or serine phosphorylated derivatives of such BAD polypeptides as well as the encoding DNA sequences.

Polynucleotides encoding BAD polypeptides having substitutions for serines corresponding to Serine-112 and/or Serine-136 or fragments or analogs thereof, may include sequences that facilitate transcription (expression sequences) and translation of the coding sequences, such that the encoded polypeptide product is produced. Construction of such polynucleotides are described further in Maniatis et al. (See Sambrook et al., supra). For example, but not a limitation, such polynucleotides can include a promoter, a transcription termination site (polyadenylation site in eukaryotic expression hosts), a ribosome binding site, and, optionally, an enhancer for the use in eukaryotic expression hosts, and, optionally, sequences necessary for replication of a vector. A typical eukaryotic expression cassette will include a polynucleotide sequence encoding a BAD polypeptide linked downstream (i.e., in translational reading frame orientation; polynucleotide linkage) of a promoter such as the HSV tk promoter or the pgk (phosphoglycerate kinase) promoter, optionally linked to an enhancer and a downstream polyadenylation site (e.g., an SV40 large T Ag poly A addition site).

Preferably, the amino acid sequences of BAD polypeptides and mutant forms thereof occur in the given order and may comprise other intervening and/or terminal sequences; generally such polypeptides are less than 1000 amino acids in length, more usually less than about 500 amino acids in length, and still more preferably approximately 200 amino acids in length. In particular, the murine BAD polypeptide and the corresponding mutant BAD polypeptides having amino acid substitutions for the serine 112 and/or serine 136 have 204 amino acids in length.

The degeneracy of the genetic code gives a finite set of polynucleotide sequences encoding these amino acid sequences; this set of degenerate sequences may be readily generated by hand or by computer using commercially available software. Isolated BAD polynucleotides typically are less than approximately 10,000 nucleotides, more preferably less than approximately 3,000 nucleotides, still more preferably less than approximately 1,500 nucleotides, and most preferable approximately 600 nucleotides.

The BAD polynucleotides from which the mutant BAD polynucleotides are made can be identified by virtue of their hybridization to BAD RNA or DNA sequences under stringency conditions in which the polynucleotides encoding BCL-2 do not hybridize with the BAD polynucleotides.

Mutant bad polynucleotides may be short oligonucleotides such as for example 20–100 bases long which are fragments of the full-length mutant bad polynucleotide and which encodes a mutant BAD polypeptide which is able to exert an apoptotic effect. Mutant bad polynucleotide sequences may also comprise part of a larger polynucleotide, for example, a cloning vector comprising a BAD clone and may be fused, by polynucleotide linkage, in frame with another polynucleotide sequence encoding a different protein such as, for example, a polynucleotide encoding a mutant BAD polypeptide linked to a heterologous peptide such as a Tat peptide (YGRKKRRQRRRG, SEQ ID NO:50) which facilitates intracellular delivery of the BAD polypeptide or mutant BAD polypeptide. Similarly, the encoded polypeptide can be a fusion protein comprising a mutant BAD polypeptide and a heterologous protein such as the Tat polypeptide (YGRKKRRQRRRG, SEQ ID NO:50).

Typically, mutant bad polynucleotides comprise at least 25 consecutive nucleotides which are substantially identical to a naturally-occurring BAD sequence and having a codon for an amino acid substitution of the serine at position 112 or the serine at position 136 in the encoded polypeptide, more preferably the mutant BAD polynucleotides comprise at least 50 to 100 consecutive nucleotides and still more preferably at least 500 to 550 consecutive nucleotides.

Additionally, a mutant bad cDNA can be used to construct transgenes for expressing mutant BAD polypeptides at high levels and/or under the transcriptional control of transcription control sequences which do not naturally occur adjacent to the BAD gene. For example, a constitutive promoter (e.g., a HSV-tk or pgk promoter) or a cell-lineage specific transcriptional regulatory sequence (e.g., a CD4 or CD8 gene promoter/enhancer) may be operably linked to a BAD-encoding polynucleotide sequence to form a transgene (typically in combination with a selectable marker such as a neo gene expression cassette). Such transgenes can be introduced into cells such as hematopoietic stem cells and transgenic cells and transgenic nonhuman animals can be obtained according to conventional methods. Transgenic cells and/or transgenic nonhuman animals may be used to generate models of diseases involving overexpression or inappropriate expression of BAD and to screen for agents to treat such diseases as, for example, immunodeficiency diseases, including AIDS, senescence, neurodegenerative disease, ischemic and reperfusion cell death, infertility, wound-healing, and the like.

The term "naturally-occurring" as used herein in reference to BAD or serine phosphorylated BAD or other BCL-2 family members is intended to mean a polynucleotide or polypeptide that can be found in nature and present in an organism (including viruses) although not necessarily in a discrete or isolated form, which can be isolated from a source in nature and which has not been intentionally modified by man in the laboratory.

The BAD polypeptides and mutant BAD polypeptides of the present invention (including serine-phosphorylated BAD) in one embodiment are provided in isolated and purified form. By "pure form" or "purified form" or "substantially purified form" it is meant that the object species such as a BAD polypeptide is substantially free of other substances which are not the object species. Generally a substantially pure composition will comprise more than about 80 to 90 percent of all macromolecular species present in the composition. Most preferably, the object species is purified to essential homogeneity such that contaminant species cannot be detected in the composition by conventional detection methods and wherein the composition consists essentially of a single macromolecular species. Solvent species, small molecules (<500 Daltons), and elemental ion species are not considered macromolecular species.

In another embodiment the present invention provides a method for producing a BAD polypeptide with increased death agonist activity. The method comprises preparation of a mutant BAD polypeptide having substitutions at the Serine-112 and/or Serine-136 positions in which the amino acid at said position is an amino acid other than serine. The mutant BAD polypeptide can be made based upon the sequence of a BAD polypeptide from any source including a human BAD polypeptide the partial sequence of which is set forth in SEQ ID NO:54. In such a BAD polypeptide the serine-112 and serine-136 residues are identified by virtue of alignment with murine BAD as set forth in SEQ ID NO:1. The derived sequence having amino acid substitution and the 112 and/or 136 positions can then be prepared by any of a number of methods.

For example, a mutant BAD polypeptide may be made by expression of the DNA sequences encoding the mutant BAD polypeptide in a suitable transformed host cell. Using methods well known in the art, the DNA encoding the mutant BAD can be prepared and linked to an expression vector, transformed into a host cell and conditions established that are suitable for expression of the mutant BAD polypeptide by the transformed cell.

Any suitable expression vector may be employed to produce recombinant the mutant BAD polypeptide such as, for example, the mammalian expression vector pCB6 (Brewer, *Meth Cell Biol* 43:233–245, 1994 which is incorporated by reference) or the *E. coli* pET expression vectors, specifically, pET-30a (Studier et al., *Methods Enzymol* 185:60–89, 1990 which is incorporated by reference). Other suitable expression vectors for expression in mammalian and bacterial cells are known in the art as are expression vectors for use in yeast or insect cells. Baculovirus expression systems can also be employed. Mutant BAD polypeptides can also be prepared by chemical synthesis, by expression in in vitro translation systems using polynucleotide template or by isolation from biological samples. Chemical synthesis of a peptide can be performed, for example, by the classical Merrifeld method of solid phase peptide synthesis (Merrifeld, *J Am Chem Soc* 85:2149, 1963 which is incorporated by reference) or the FMOC strategy on a Rapid Automated Multiple Peptide Synthesis system (DuPont Company, Wilmington, Del.) (Caprino and Han, *J Org Chem* 37:3404, 1972 which is incorporated by reference).

Fragments or analogs of a mutant BAD polypeptide can also be made. A fragment of a BAD polypeptide is a polypeptide that has an amino-terminal and/or carboxy-terminal deletion, but where the remaining amino acid sequence is identical to the corresponding positions in the sequence of the full-length BAD polypeptide. Fragments are at least 10 amino acids long, preferably at least 20 amino acids long and most preferably at least 50 amino acids long or longer up to the length of a full-length naturally-occurring BAD polypeptide. The term "analog", "mutein" or "mutant" as used herein refers to polypeptides which are comprised of a segment of at least 10 amino acids that has substantial identity to a portion of the naturally-occurring protein. Typically, analog polypeptides comprise a conservative amino acid substitution (or addition or deletion) with respect to the naturally-occurring sequence or the serine-112 and or serine-136 substituted mutants. Analogs typically are at least 20 amino acids long, preferably at least 50 amino acids long or longer up to the length of a full-length naturally-occurring BAD polypeptide.

The discovery of the inhibitory effect of the phosphorylation of BAD on the binding of BAD to BCL-$X_L$ provides a new site for intervention in the modulation of apoptosis. Such intervention can involve the administration of a mutant BAD polypeptide having an amino acid other than serine at positions 112 and/or position 136 or a substantially identical mutein, fragment, analog, or fusion protein thereof.

Modulation of the phosphorylation of BAD within a cell can be accomplished by altering the intracellular phosphorylation state of the BAD polypeptide. The phosphorylation state of many proteins are dynamically controlled by both protein kinases and protein phosphatases (Cohen, *Ann Rev Biochem* 58:453–508, 1989 which is incorporated by reference). The present work shows that both protein kinases and a protein phosphatase can alter the phosphorylation state of BAD.

Protein phosphatases that dephosphorylate serine residues in proteins have been extensively studied and both inhibitors and activators have been reported (for reviews, see Wera and Hemmings, *Biochem J* 311:17–29, 1995; Shenolikar, *Cancer Biol* 6:219–227, 1995 which are incorporated by reference). Thus, either inhibitors or activators can be administered which act to diminish or increase the action of intracellular phosphatase to remove the phosphate from either or both serine-112 and serine-136 of BAD. Many phosphatase inhibitors and activators are known and these can be readily screened by one skilled in the art for activity, for example, by determining the effect of a test agent on the in vitro or in vivo cleavage of a radiolabeled phosphate group from serines 112 or 136 of BAD by phosphatase activity. (see, for example, Matthews, *Pharmac Ther* 67:323–350, 1995; Shenolikar, supra, which are incorporated by reference). It is preferred that the inhibitors and activators have selective actions on the phosphatase(s) acting upon BAD.

Similarly, inhibitors and activators of protein kinases are known and can be used as therapeutic agents (for example, see Levitski, *Eur J Biochem* 226:1–13, 1994 which is incorporated by reference). Thus, either kinase inhibitors or activators can be administered which act to increase or diminish the action of intracellular kinases which phosphorylate BAD at either or both serine 112 and serine 136 of BAD. It is preferred that the inhibitors and activators have selective actions on the kinase(s) acting upon BAD. In the present study it is shown that kinases act selectively in that neither phosphokinase C (PKC) nor RAF1 could phosphorylate BAD on serine 112 or serine 136 in vitro, however, HMK (heart muscle kinase, a form of phosphokinase A) could. Thus, inhibitors and activators effective in modulating the phosphorylation state of BAD could be tested for their effect of BAD phosphorylation in vitro using heart muscle kinase for example as a selective serine-112 kinase. Alternatively, in vivo testing could be done using a number of experimental approaches, and one example, as reported herein, utilizes the endogenous phosphorylation of BAD upon readdition of IL-3 after withdrawal for two hours. Such standard testing systems could be used to test candidate compounds as inhibitors or activators of BAD phosphorylation. As shown in the present studies, PMA effectively promoted BAD phosphorylation and Staurosporin inhibited BAD phosphorylation.

It may be desirable to modulate or decrease the amount of BAD that is able to bind to BCL-$X_L$ in the cells. Such as in the treatment of diseases involving overexpression or inappropriate expression of BAD or the active form of BAD at any level for which decreasing the amount of BAD can interfere with apoptosis and promote cell survival. In such disease conditions, treatments to modulate or decrease non-phosphorylated BAD can be used. Such treatments can involve administration of BAD serine phosphatase inhibitors or serine 112/serine 136 kinase activators to decrease the ability of BAD to bind to BCL-$X_L$. Such treatment would be useful in diseases such as immunodeficiency diseases, senescence, neurodegenerative disease, ischemic cell death, reperfusion cell death, infertility and wound-healing.

Conversely, in the treatment of diseases involving under-expression or inappropriately low levels of active BAD, it may be desirable to increase the amount of BAD that is able to bind to BCL-$X_L$ in the cells. In such disease conditions, treatments to modulate or increase the non-phosphorylated, active BAD can be used. Such treatments can involve administration of BAD serine phosphatase activators or serine-112/serine-136 kinase inhibitors to increase the ability of BAD to bind to BCL-$X_L$. Such treatment would be useful in diseases such as cancer, viral infections, lymphoproliferative conditions, arthritis, infertility, inflammation and autoimmune diseases.

BAD polypeptides and mutant BAD polypeptides of the present invention can be prepared by chemical synthesis, in recombinant cells transformed with a polynucleotide encoding a BAD polypeptide, by expression in in vitro translation systems using polynucleotide template or by isolation from biological samples. Phosphorylation of amino acid residues such as to produce the phosphorylated serine containing polypeptides can be accomplished by known methods generally in the amino acid prior to polypeptide synthesis but in some other methods after synthesis of the polypeptide such as is demonstrated herein with use of a kinase such as HMK.

Derivitives can include non-peptidal substances possessing the biological properties of BAD polypeptides, mutant BAD polypeptides or phosphorylated BAD polypeptides or fragments thereof in eliciting an apoptotic state and/or in binding to 14-3-3 protein. The techniques for making peptide mimetics are well known in the art. (See for example, Navia and Peattie, *Trends Pharm Sci* 14:189–195, 1993; Olson et al, *J Med Chem* 36:3039–3049 which are incorporated by reference). Typically this involves identification and characterization of the protein target site as well as the protein ligand using X-ray crystallography and nuclear magnetic resonance technology. The amino acid sequence of the BAD polypeptide which contains BH1 and BH2 regions and the phosphorylation sites at serine residues 112 and 136 have been identified. Using this information along with computerized molecular modeling, a pharmacophore hypothesis can be developed and compounds are made and tested in an assay system.

The BAD polypeptides of the present invention can also be used to detect new polypeptides as well as non-peptide compositions capable of associating or binding to the 14-3-3 protein to serve as antagonists to the binding of BAD to 14-3-3 using a standard radioligand assay system. (For example, see Bylund and Toews, *Am J Physiol* 265:L421–429, 1993 which is incorporated by reference). Such antagonists could serve to remove any protective or sequestering effect that the binding to 14-3-3 might have. In one embodiment, the antagonist can also be polypeptides containing conserved serine phosphorylated motifs as described above including serine phosphorylated BAD polypeptides or fragments thereof. It is also possible to utilize as antagonists polypeptides having a modified or substituted amino acid or non-amino acid residue at positions 112 and/or 136 in place of a serine residue such that the polypeptide containing the modified amino acid or non-amino acid residue functions in the same way as a phosphoserine containing BAD polypeptides to bind 14-3-3 and displace phosphorylated BAD polypeptide.

The radioligand assays useful in screening for antagonists to the binding of BAD to 14-3-3 can involve the preparing a radiolabeled form of the BAD polypeptide or fragment thereof capable of binding to a 14-3-3 protein using, for example, either a $^3$H or $^{125}$I according to standard methods. For example, the Bolton Hunter Reagent can be used (ICN Chemicals, Radioisotope Division, Irvine, Calif.). The radiolabeled BAD ligand binds to the 14-3-3 protein immobilized to a substrate such as in a standard ELISA-style plate assay. The amount of bound and/or free radiolabeled ligand is then measured. (For example see Slack et al. *BioTechniques* 7:1132–1138, 1989; Dower et al, *J Immunol* 142:4314–4320, 1989 which are incorporated by reference). Alternatively, the 14-3-3 protein can be radiolabeled and the BAD polypeptide immobilized to a substrate. In a variation to this approach, the binding assay is performed with soluble, non-immobilized BAD polypeptide and 14-3-3 protein. Competitive inhibition of the binding of the radiolabeled BAD ligand to the 14-3-3 protein on addition of a test compound can be evaluated by standard methods of analysis. (For example, see Rovati, *Pharmacol Res* 28:277–299, 1993 which is incorporated by reference).

The present invention also includes therapeutic or pharmaceutical compositions comprising an active agent which is a phosphatase inhibitor or activator or a kinase inhibitor or activator or a BAD polypeptide or a mutant BAD polypeptide or a phosphorylated BAD for treating diseases or disease conditions in which the propensity for cell death can be advantageously modulated and methods therefor. These compositions and methods are useful for treating a number of diseases such as, for example, neoplasia, certain viral infections (e.g. Epstein-Barr virus), lymphoproliferative conditions, arthritis, inflammation, autoimmune diseases and the like resulting from an inappropriate decreased cell death as well as diseases such as, for example, immunodeficiency diseases, senescence, neurodegenerative disease, ischemic cell death, reperfusion cell death, infertility, wound-healing and the like resulting from an inappropriate increase in cell death. Treatment can also involve administration to affected cells ex vivo.

The therapeutic or pharmaceutical compositions of the present invention can be administered by any suitable route known in the art including for example intravenous, subcutaneous, intramuscular, transdermal, intrathecal or intracerebral or administration to cells in ex vivo treatment protocols. Administration can be either rapid as by injection or over a period of time as by slow infusion or administration of slow release formulation. For treating tissues in the central nervous system, administration can be by injection or infusion into the cerebrospinal fluid (CSF). When it is intended that the active agent be administered to cells in the central nervous system, administration can be with one or more agents capable of promoting penetration of the active agent across the blood-brain barrier. (See for example, Friden et al., *Science* 259:373–377, 1993 which is incorporated by reference). Furthermore, BAD, mutant BAD polypeptides and serine-phosphorylated BAD polypeptides can be stably linked to a polymer such as polyethylene glycol to obtain desirable properties of solubility, stability, half-life and other pharmaceutically advantageous properties. (See for example Davis et al. *Enzyme Eng* 4:169–73, 1978; Burnham, *Am J Hosp Pharm* 51:210–218, 1994 which are incorporated by reference).

Furthermore, the active agent can be in a composition which aids in delivery into the cytosol of a cell. For example, the peptide may be conjugated with a carrier moiety such as a liposome that is capable of delivering the peptide into the cytosol of a cell. Such methods are well known in the art (for example see Amselem et al., *Chem Phys Lipids* 64:219–237, 1993 which is incorporated by reference). Alternatively, the active agent can be modified to include specific transit peptides or fused to such transit peptides which are capable of delivering the BAD polypeptide or mutant BAD polypeptide into a cell. In addition, the polypeptide can be delivered directly into a cell by microinjection.

The phosphatase inhibitors and activators and kinase inhibitors and activators can also be linked or conjugated with agents that provide desirable pharmaceutical or pharmacodynamic properties as described above such as the coupling of the active substance to a compound which promotes penetration or transport across the blood-brain barrier or stably linking the active substance to a polymer to obtain desirable properties of solubility, stability, half-life and the like.

The compositions are usually employed in the form of pharmaceutical preparations. Such preparations are made in a manner well known in the pharmaceutical art. One preferred preparation utilizes a vehicle of physiological saline solution, but it is contemplated that other pharmaceutically acceptable carriers such as physiological concentrations of other non-toxic salts, five percent aqueous glucose solution, sterile water or the like may also be used. It may also be desirable that a suitable buffer be present in the composition. Such solutions can, if desired, be lyophilized and stored in a sterile ampoule ready for reconstitution by the addition of sterile water for ready injection. The primary solvent can be aqueous or alternatively non-aqueous. The active agent can also be incorporated into a solid or semi-solid biologically compatible matrix which can be implanted into tissues requiring treatment.

The carrier can also contain other pharmaceutically-acceptable excipients for modifying or maintaining the pH, osmolarity, viscosity, clarity, color, sterility, stability, rate of dissolution, or odor of the formulation. Similarly, the carrier may contain still other pharmaceutically-acceptable excipients for modifying or maintaining release or absorption or penetration across the blood-brain barrier. Such excipients are those substances usually and customarily employed to formulate dosages for parenteral administration in either unit dosage or multi-dose form or for direct infusion by continuous or periodic infusion.

Dose administration can be repeated depending upon the pharmacokinetic parameters of the dosage formulation and the route of administration used.

It is also contemplated that certain formulations containing the active agent are to be administered orally. Such formulations are preferably encapsulated and formulated with suitable carriers in solid dosage forms. Some examples of suitable carriers, excipients, and diluents include lactose, dextrose, sucrose, sorbitol, mannitol, starches, gum acacia, calcium phosphate, alginates, calcium silicate, microcrystalline cellulose, polyvinylpyrrolidone, cellulose, gelatin, syrup, methyl cellulose, methyl- and propylhydroxybenzoates, talc, magnesium, stearate, water, mineral oil, and the like. The formulations can additionally include lubricating agents, wetting agents, emulsifying and suspending agents, preserving agents, sweetening agents or flavoring agents. The compositions may be formulated so as to provide rapid, sustained, or delayed release of the active ingredients after administration to the patient by employing procedures well known in the art. The formulations can also contain substances that diminish proteolytic degradation and/or substances which promote absorption such as, for example, surface active agents.

The specific dose is calculated according to the approximate body weight or body surface area of the patient or the volume of body space to be occupied. The dose will also be calculated dependent upon the particular route of administration selected. Further refinement of the calculations necessary to determine the appropriate dosage for treatment is routinely made by those of ordinary skill in the art. Such calculations can be made without undue experimentation by one skilled in the art in light of the activity disclosed herein in assay preparations of target cells. Exact dosages are determined in conjunction with standard dose-response studies. It will be understood that the amount of the composition actually administered will be determined by a practitioner, in the light of the relevant circumstances including the condition or conditions to be treated, the choice of composition to be administered, the age, weight, and response of the individual patient, the severity of the patient's symptoms, and the chosen route of administration. Whereas typically the patient as referenced herein is human, nevertheless, the formulations and methods herein can be suitably prepared and used for veterinary applications in addition to human applications and the term "patient" as used herein is intended to include human and veterinary patients.

In a number of circumstances it would be desirable to determine the levels of a phosphorylated BAD polypeptide with respect to the non-phosphorylated BAD in a cell. This would provide an assessment of the apoptotic status of the cell and allow the design of a rational treatment program designed to change the levels and/or ratio of phosphorylated to non-phosphorylated BAD. High levels of non-phosphorylated BAD or a high ratio of non-phosphorylated BAD to phosphorylated BAD might indicate an increased state of apoptosis in the cell and treatment to decrease the non-phosphorylated BAD or the ratio might be indicated. Conversely, low levels of non-phosphorylated BAD or a low ratio might indicate the need to increase either the non-phosphorylated BAD or the ratio.

Furthermore, in the treatment of disease conditions, compositions containing BAD can be administered exogenously and it would likely be desirable to achieve certain target levels of BAD polypeptide as well as ratio of non-phosphorylated to phosphorylated BAD in sera, in any desired tissue compartment or in the affected cells or tissue. It would, therefore, be advantageous to be able to monitor the levels of non-phosphorylated and phosphorylated BAD polypeptide in a patient or in a biological sample including a tissue biopsy sample obtained form a patient and, in some cases, it might also be desirable to monitor the levels of other BCL-2 family members including the BAD partners, BCL-2 and BCL-$X_L$. Accordingly, the present invention also provides methods for detecting the presence of BAD and the ratio of non-phosphorylated to phosphorylated BAD in a cell or a population of cells or in a sample from a patient.

The term "detection" as used herein in the context of detecting the presence of non-phosphorylated and phosphorylated BAD in a patient is intended to include the determining of the amount of non-phosphorylated and phosphorylated BAD or the ability to express and/or post-translationally modify BAD, the distinguishing of non-phosphorylated and phosphorylated forms of BAD from each other and from other BCL-2 family members, the estimation of prognosis in terms of probable outcome of a disease involving non-phosphorylated and phosphorylated BAD and the prospect for recovery, the monitoring of non-phosphorylated and phosphorylated levels of BAD over a period of time as a measure of status of the condition, and the monitoring of phosphorylated and phosphorylated levels of BAD for determining a preferred therapeutic regimen for the patient.

To detect the presence and levels of non-phosphorylated and phosphorylated BAD in a cell or population of cells or patient, a sample is obtained from the population of cells or from the patient. The sample can be a population of cells, a tissue biopsy sample or a sample of blood, a cell fraction from blood, plasma, serum, CSF or the like. When the sample is from a patient any of a variety of tissues known to express BAD can serve as the source of cells for testing as can a sample or biopsy from a diseased tissue such as a neoplasia. When assessing peripheral levels of BAD polypeptide, the sample can be a sample of a cells obtained from blood or a cell-free sample such as plasma or serum.

The present invention further provides for methods to detect the presence of the non-phosphorylated and phosphorylated forms of BAD polypeptide in a sample obtained from a patient. Any method known in the art for detecting proteins can be used. Such methods include, but are not limited to immunodiffusion, immunoelectrophoresis, immunochemical methods, binder-ligand assays, immunohistochemical techniques, agglutination and complement assays. (for example see *Basic and Clinical Immunology*, Sites and Terr, eds., Appleton & Lange, Norwalk, Conn. pp 217–262, 1991 which is incorporated by reference). Preferred are binder-ligand immunoassay methods including reacting antibodies with an epitope or epitopes of the BAD polypeptide and competitively displacing a labeled BAD polypeptide or derivative thereof. The measurement of levels of phosphorylated BAD can be by any of a variety of methods. A particularly useful method based upon the work reported herein would involve determination of the amount of phosphorylated BAD bound to 14-3-3 protein. This can be done by immunoprecipitation and Western blot analysis using anti-BAD, anti-serine-phosphorylated-BAD and anti14-3-3 antibodies both of which can be prepared by known methods. Alternatively, phosphorylated and unphosphorylated BAD can be determined by using anti-BAD and anti-serine-phosphorylated-BAD antibodies in an immunoassay method as described below.

Polyclonal antibodies can be prepared by immunizing rabbits or other animals by injecting antigen followed by subsequent boosts at appropriate intervals. The animals are bled and sera assayed against purified BAD polypeptide usually by ELISA or by bioassay based upon the ability to accelerate apoptosis in cells. Monoclonal antibodies can be prepared after the method of Milstein and Kohler by fusing splenocytes from immunized mice with continuously replicating tumor cells such as myeloma or lymphoma cells. (Milstein and Kohler *Nature* 256:495–497, 1975; Gulfre and Milstein, *Methods in Enzymology: Immunochemical Techniques* 73:1–46, Langone and Banatis eds., Academic Press, 1981 which are incorporated by reference). The hybridoma cells so formed are then cloned by limiting dilution methods and supernates assayed for antibody production by ELISA, RIA or bioassay.

Numerous competitive and non-competitive protein binding immunoassays are well known in the art. Antibodies employed in such assays may be unlabeled, for example as used in agglutination tests, or labeled for use in a wide variety of assay methods. Labels that can be used include radionuclides, enzymes, fluorescers, chemiluminescers, enzyme substrates or co-factors, enzyme inhibitors, particles, dyes and the like for use in radioimmunoassay (RIA), enzyme immunoassays, e.g., enzyme-linked immunosorbent assay (ELISA), fluorescent immunoassays and the like. Polyclonal or monoclonal antibodies to a BAD polypeptide or an epitope thereof can be made for use in immunoassays by any of a number of methods known in the art.

Preferred embodiments of the invention are described in the following examples. Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims which follow the examples.

EXAMPLE 1

This example illustrates that BAD and 14-3-3 protein can be co-immunoprecipitated from cells expressing both proteins.

Plasmid pGEX-3X-HMK-BAD was constructed by introducing a DNA sequence encoding the amino acid sequence RRASV, the heart muscle kinase (HMK) phosphorylation target sequence, by PCR in between the BamHI and EcoRI sites of pGEX-3X, then cloning the BAD cDNA in frame into the EcoRI site. This plasmid produces a BAD protein which is fused to a glutathione-S-transferase protein by the HMK amino acid sequence. The resulting protein was designated GST-BAD. GST-BAD was purified after overexpression in $E.$ $Coli$ by standard methods using GST agarose. Purified GST-BAD protein was labeled in vitro with $[\gamma^{32}P]ATP$ and heart muscle kinase to produce GST-BAD-$^{32}PO_4$. A 16 day embryonic mouse EXlox cDNA expression library was screened for clones which produced protein which bound to GST-BAD-$^{32}PO_4$. Two independent clones of the tau form ($\tau$) of 14-3-3 (Neilsen, $Biochem.$ $et$ $Biophys.$ 1088:425–428, 1991 which is incorporated by reference) were identified and the DNA sequence was determined. The predicted protein sequence deduced from the DNA sequence of this murine gene proved to be equivalent to a previously cloned human homolog, except for an Asp143Glu substitution. Muslin et al. ($Cell$ 84:889–897, 1996 which is incorporated by reference) demonstrated that 14-3-3 is a specific phosphoserine binding protein, thus phosphorylation of a serine within the HMK motif could conceivably have mediated the binding of GST-BAD-$^{32}PO_4$ to the 14-3-3$\tau$ clones identified from the mouse expression library. The inventors assessed whether a BAD/14-3-3$\tau$ interaction occurred in vivo.

For metabolic labeling, cells were labeled either in phosphate free RPMI1640 media with $[^{32}P]$-orthophosphate or $[^{33}P]$-orthophosphate (1 mCi/$10_6$ cells) or in methionine-free RPMI1640 media with $[^{35}S]$-methionine (200 mCi/$10_6$ cells) for 4 hr. Cells were lysed either in 137 mM NaCl, 20 mM Tris (pH 8.0), 1.5 mM MgCl$_2$, 1 mM EDTA, 50 mM NaF, 0.2%–0.5% NP40 containing aprotinin (0.15 U/ml), 20 mM leupeptin, and 1 mM phenylmethysulfonyl fluoride for co-immunoprecipitation, or in RIPA buffer for direct immunoprecipitation. Lysates were first cleared with protein A beads for 30 min, followed by incubation with antibody for 1.5 hour on ice. Finally, the antibody complexes were captured with protein A beads for 1 hour. The immunoprecipitate was washed with 0.2% NP-40 lysis buffer, resuspended in loading buffer, and separated by SDS-PAGE. The gels were treated with fluorography and visualized by autoradiography or were transferred to a nitrocellulose membrane for further immunoblot analysis. For western blots, lysates were separated by SDS-PAGE, and transferred to a nitrocellulose membrane. The membrane was first blocked with 3% milk solution for 1 hour, followed by incubation with primary and secondary antibodies for one hour each, and finally developed by enhanced chemiluminescence using a kit supplied by Amersham. HA14-3-3$\tau$ was immunoprecipitated with a mouse anti-hemagglutinin monoclonal antibody (12CA5) at 1:50 dilution.

Plasmids capable of expressing wild type BAD (pSSFV-BAD) or an influenza virus hemagglutinin-14-3-3$\tau$ fusion protein (pSSFV-HA14-3-3$\tau$) were constructed by cloning a wild type BAD cDNA into the EcoRI site of the vector pSSFV or by incorporating the hemagglutinin (HA) epitope in frame into the 5' end of the 14-3-3$\tau$ cDNA and then cloning the fusion into the EcoRI site of pSSFV. FL5.12 cells, which are dependent on IL-3 for survival, were cotransformed with these plasmids by electroporation at 200 V and 900 pF, and plated 48 hours later at limited dilution in media containing 2 mg/ml G418 in 96-well microtiter plates. Single-cell originated clones which were expressing both proteins as judged by western blot analysis were selected after 7–10 days. Lysates from cells expressing both BAD and HA14-3-3$\tau$ were analyzed by western. An anti-BAD rabbit polyclonal antibody (10929, 1:1000) revealed that BAD migrated as a doublet of approximately $^{24}\!/_{25}$ kD (FIG. 1$a$). This doublet is also present in cells that express BAD but no HA14-3-3$\tau$ (data not shown). Immunoprecipitation of HA14-3-3$\tau$ with an anti-hemagglutinin monoclonal antibody (12CA5, 1:50) resulted in the co-precipitation of both BAD species.

A hamster monoclonal antibody specific for mouse BAD (2G11, 1:50) was prepared and utilized in a reciprocal immunoprecipitation. This demonstrated that HA14-3-3$\tau$ co-precipitated with BAD (FIG. 1$b$). When $^{35}S$-labeled FL5.12 HA14-3-3$\tau$/BAD cells were immunoprecipitated with the 2G11 anti-BAD monoclonal antibody, additional proteins of appropriate size for endogenous 14-3-3 and HA14-3-3$\tau$ were co-precipitated (FIG. 1$c$). Western blot analysis of this immunoprecipitate with an anti-14-3-3 polyclonal antibody (anti-beta/zeta 14-3-3 antibody, Upstate Biotechnology Inc.) confirmed their identity as 14-3-3 (FIG. 1$d$). The 14-3-3 interaction does not appear to be restricted to the $\tau$ isoform since BAD interacts with endogenous 14-3-3 species within FL5.12 cells as well.

EXAMPLE 2

This example illustrates the serine phosphorylation of BAD in vivo.

Figure 2A:
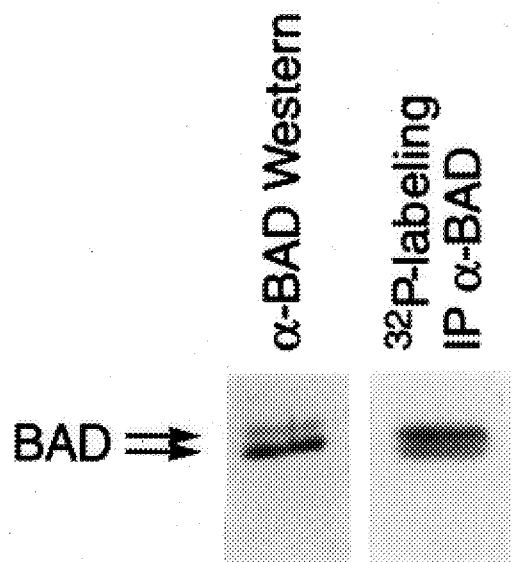
FIG. 2 illustrates (FIG. 2A) an anti-BAD western blot and autoradiograph of anti-BAD immunoprecipitated $^{32}$P-labeled BAD from FL5.12 cells coexpressing BCL-$X_L$ and BAD, (FIG. 2B) an autoradiograph of immunoprecipitated $^{32}$P-labeled BAD protein untreated, potato acid phosphatase (PAP) treated, or treated with PAP and PAP inhibitors, and (FIG. 2C) phosphoamino acid map of immunoprecipitated $^{32}$P-labeled BAD protein digested with trypsin and acid hydrolyzed showing $^{32}$P labeled serine.

FL5.12 cells expressing BAD from pSSFV-BAD were labeled with $[^{32}P]$-orthophosphate, lysed, and immunoprecipitated with hamster anti-BAD monoclonal antibody 2G11, resolved on an SDS-PAGE gel, and analyzed by fluorography as in Example 1. Alternatively, a sample of the labeled cell lysate was analyzed by western blot with a rabbit anti-BAD antibody as in Example 1. Both bands of the BAD doublet proved to be phosphorylated (FIG. 2A, lane 2). However, as compared to an immunoblot, the upper band was hyperphosporylated, while the lower band was hypophosphorylated.

$[^{32}P)]BAD$ was immunoprecipitated as in Example 1 from 10×106 FL5.12 cells expressing BCL-X$_L$ and BAD.

Figure 2B:
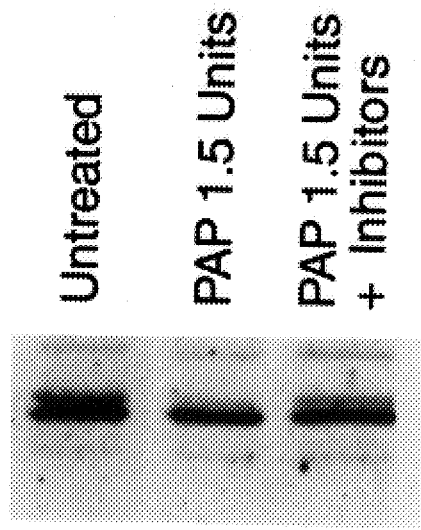

The protein A bead-BAD complexes were resuspended in 500 ml of 40 mM PIPES [piperazine-N,N'-bis(2-thansulfonic acid)] buffer (pH 6.0) containing 1 mM DTT, aprotinin (0.15 U/ml), 20 mM leupeptin, and 1 mM phenylmethysulfonyl fluoride. 1.5 units of potato acid phosphatase (Sigma) were added, and the samples were incubated at 37° C. for 30 minutes. Samples containing phosphatase inhibitors were supplemented with 50 mM sodium fluoride, 5 mM sodium phosphate, 10 mM sodium pyrophosphate, 10 mM ammonium molybdate, 5 mM EDTA and 5 mM EGTA. The protein A beads were pelleted by centrifugation, washed three times with NP-40 lysis buffer, resuspended in gel loading buffer, and examined by immunoblot analysis. Treatment of an immunoprecipitated BAD with potato acid phosphatase (PAP) eliminated the upper band, apparently converting it to the lower species (FIG. 2b). Thus, hyperphosphorylation of BAD is responsible for the difference in mobility of the two BAD species. The lack of a shift of the lower band following PAP treatment was the first suggestion that the lower band could be comprised of unphosphorylated as well as phosphorylated components.

Figure 2C:
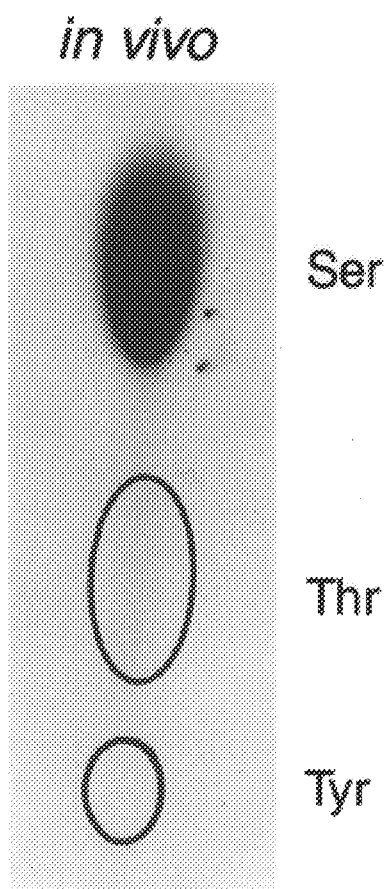

Immunoprecipitated [$^{32}$p]BAD was separated by SDS-PAGE and transferred to a nitrocellulose membrane. Membrane slices containing one or the other of the BAD species were excised, blocked in 0.5% PVP-40 (polyvinylpyrrolidone) and 0.57% acetic acid at 37° C. for 30 minutes, washed six times with water and digested with 10 mg of freshly prepared TPCK treated trypsin (Worthington Biochemicals) in 50 mM ammonium biocarbonate at 37° C. for 2 hours. The digestion was repeated for another 2 hours with fresh enzyme to ensure complete cleavage. Peptides were then dried, washed three times with water to remove ammonium biocarbonate, and then hydrolyzed in 6N HCl (Pierce) at 110° C. for 90 minutes under vacuum. Cold phosphoserine, phosphothreonine and phosphotyrosine were added to the sample, which were applied together onto a TLC plate and separated by electrophoresis utilizing a HTLE-7000 apparatus (CBS, Del Mar, Calif.) with equal volume of pH 1.9 and pH 3.5 buffers (Boyle et al., Methods Enzymol. 201:110–149, 1991 which is incorporated by reference). The location of phosphoamino acids was determined by ninhydrin staining and autoradiography. Phosphoamino acid analysis of the BAD doublet revealed that BAD was exclusively phosphorylated on serine residues (FIG. 2c).

EXAMPLE 3

This example illustrates that BAD protein can be phosphorylated in vivo at amino acid position 112 and 136.

Figures 3A, 3B, 3C:
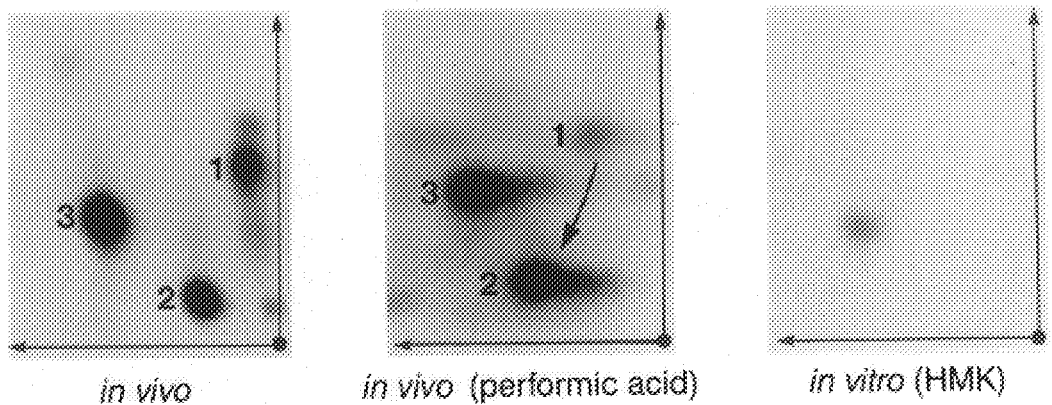
(FIG. 3B) the 2D-map of $^{32}$P-labeled, performic acid treated, tryptic peptides from in vivO $^{32}$P-phosphorylated, anti-BAD immunoprecipitated BAD.
(FIG. 3C) the 2D-map of tryptic peptides from BAD in vitro $^{32}$P-phosphorylated by heart muscle kinase.
Figure 3D:
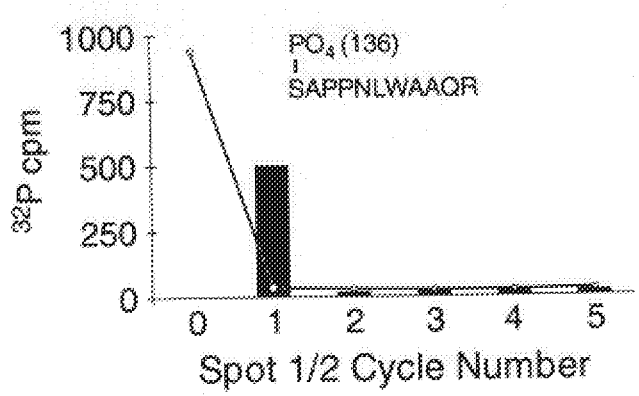
(FIG. 3D) the manual Edman degradation amino acid elution profile of tryptic peptides 1 and 2 in (FIG. 3A)
Figure 3E:
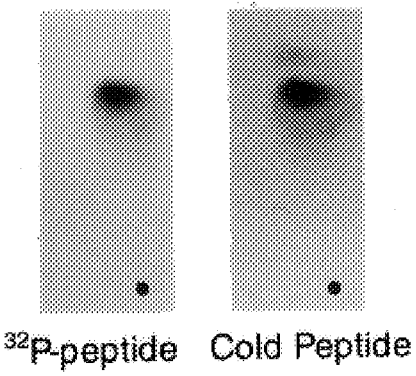
(FIG. 3E) the 2D map of a cold synthetic peptide and the $^{32}$P labeled peptide of spot 1 as in (FIG. 3A)
Figure 3F:
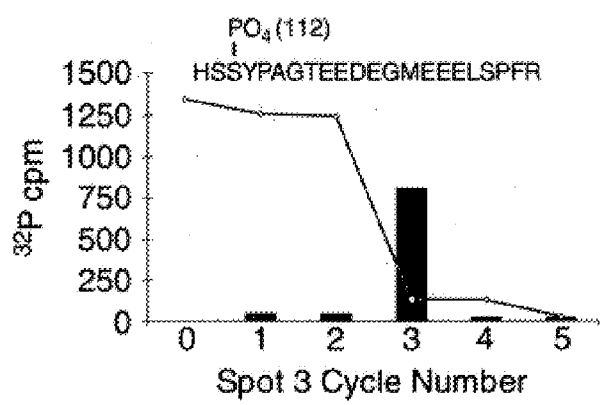
(FIG. 3F) the manual Edman degradation amino acid elution profile of tryptic peptide 3 in (FIG. 3A)
Figure 3G:
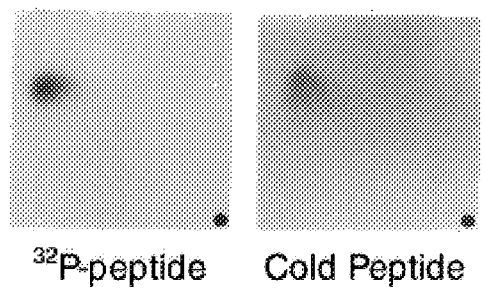
(FIG. 3G) the 2D map of a cold synthetic peptide and the $^{32}$P-labeled peptide of spot 3 as in (FIG. 3A)

Two dimensional tryptic peptidic maps of the full length upper and lower BAD proteins were generated to identify the precise sites of in vivo serine phosphorylation. BAD was immunoprecipitated from [$^{32}$P]-orthophosphate labeled cells, separated by SDS-PAGE, transferred to a nitrocellulose membrane, and digested with trypsin as in Example2. Tryptic peptides were separated in the first dimension (horizontal in FIG. 3) in pH 8.9 buffer (Boyle et al., 1991 which is incorporated by reference) by TLC utilizing a HTLE-7000 apparatus. Electrophoresis was performed for 30 minutes at 1000 V at 4° C. Separation in the second dimension (Vertical in FIG. 3) was performed by ascending chromatography in 37.5% n-butanol, 25% pyridine and 7.5% acetic acid for 10 hours. $^{32}$P-phosphopeptides were visualized by autoradiography and cold phosphopeptides were visualized with ninhydrin staining. The labeled peptides were eluted in pH 1.9 buffer from TLC plates, conjugated to Sequelon-AA membrane (Perseptive Biosystem, Framingham, Mass.) with methanol:water:triethylamine: phenylisothiocyanate (7:1:1:1) at 55° C. The digested peptides were either directly applied onto a thin layer chromatography (TLC) plate or treated with performic acid to uniformly oxidize peptides before application to the TLC plate. Peptides were separated according to charge in the first dimension, followed by hydrophobicity in the second dimension, as above. The 2D maps of the upper and lower BAD species were identical (FIG. 3a, b). Spot 1 and 2 were noted to vary in their relative proportion between various preparations. Performic acid treatment resulted in the conversion of spot 1 to spot 2 (FIG. 3a, b), suggesting that both spots were derived from the same peptide but were differentially oxidized in preparation. The $^{32}$P-labeled tryptic peptides from all three spots were subjected to manual Edman degradation performed as previously described (Boyle et al., 1991; Luo, et al., Methods Enzyml. 201:149–152, 1991 which are incorporated by reference). The $^{32}$P-labeled position of spot 1 or 2 was located at amino acid residue #1 (FIG. 3d), whereas it was located at amino acid residue #3 for spot 3 (FIG. 3f). BAD possesses five tryptic peptides with serine at position #1, and three tryptic peptides with serine at position #3. Synthetic peptides with phosphoserine replacements at the corresponding positions were generated, comigrated on TLC plates and compared with the $^{32}$P-labeled peptides isolated from spot 1 & 3. This revealed that spot 1 was a peptide with phosphorylated Ser136 (FIG. 3d, e), while spot 3 was a peptide with phosphorylated Ser112 (FIG. 3f, g). The upper band consistently displayed more $^{32}$P-cpm and a higher specific activity. This suggests that the upwards mobility shift reflects simultaneous phosphorylation of both sites, whereas the lower band would only be phosphorylated on either, single site.

A series of kinases were assessed in vitro to determine which would phosphorylate BAD protein purified from a bacterial expression system. pET-14b-BAD was constructed by cloning BAD cDNA into the BamHI site downstream of and in frame with a histidine hexapeptide encoding sequence. A His6-BAD fusion peptide was produced in E. coli and purified over a metal affinity column according to the manufacturers instructions (Novagen). Purified BAD was phosphorylated in vitro in 50 mM Tris-HCl pH 7.5, 15 mM MgCl$_2$, 0.5 mM DTT, 10 mM ATP, and 20 mCi of [$^{32}$P]-ATP in the presence of 10 units of heart muscle kinase (Sigma). The mixture was incubated at 30° C. for 15 minutes. Kinase assays were terminated by adding EDTA and incubating at 70° C. for 15 minutes. Tryptic peptides were then generated and subjected to two dimensional electrophoresis and visualized by autoradiography as in Example 2. RAF1, PKC and heart muscle kinase (HMK) could phosphorylate BAD in vitro (data not shown), but only HMK phosphorylated BAD at one of the correct sites, Ser112 (FIG. 3c). Thus, BAD is phosphorylated at two serine residues in vivo, corresponding to amino acid positions 112 and 136.

EXAMPLE 4

This example illustrates that BAD hyperphosphorylation is promoted by IL-3, hyperphosphorylated BAD coimmunoprecipitates with BCL-X$_L$, and kinase activators enhance and inhibitors suppress BAD hyperphosphorylation.

FL5.12 cells co-expressing BCL-X$_L$ and BAD are dependent upon IL-3 for their survival. The inventors tested whether withdrawal and readdition of IL-3 would affect BAD phosphorylation. IL-3 was withdrawn from cells for two hours (-IL-3), followed by the readdition of IL-3 for fifteen minutes (+IL-3). Cells were washed with PBS twice, resuspended in Buffer A (10 mM Tris pH 7.5, 25 mM NaF, 5 mM MgCl$_2$, 1 mM EGTA, 1 mM DTT, aprotinin 0.15 U/ml, 20 mM leupeptin, 1 mM PMSF) and incubated on ice for fifteen minutes. Cells were then homogenized in a Dounce homogenizer with fifty strokes and nuclei were removed by centrifugation at 500 g for ten minutes. The supernatant was further centrifuged at 315,000 g for thirty minutes to separate cytosol from crude membranes. Membrane fractions were solubilized in 1% SDS and centrifuged at 12,000 g for five minutes at room temperature. Supernatants or cytosol fractions were diluted 1:10 in 1% Triton X-100, 100 mM NaCl in buffer A and proteins were selectively immunoprecipitated as in Example 1. A mouse anti-human BCL-X$_L$ monoclonal antibody (7B2, Boise et al., *Immunity* 3:87–98, 1995) was used to immunoprecipitate BCL-X$_L$ and BCL-X$_L$ complexes.

Figure 4A:
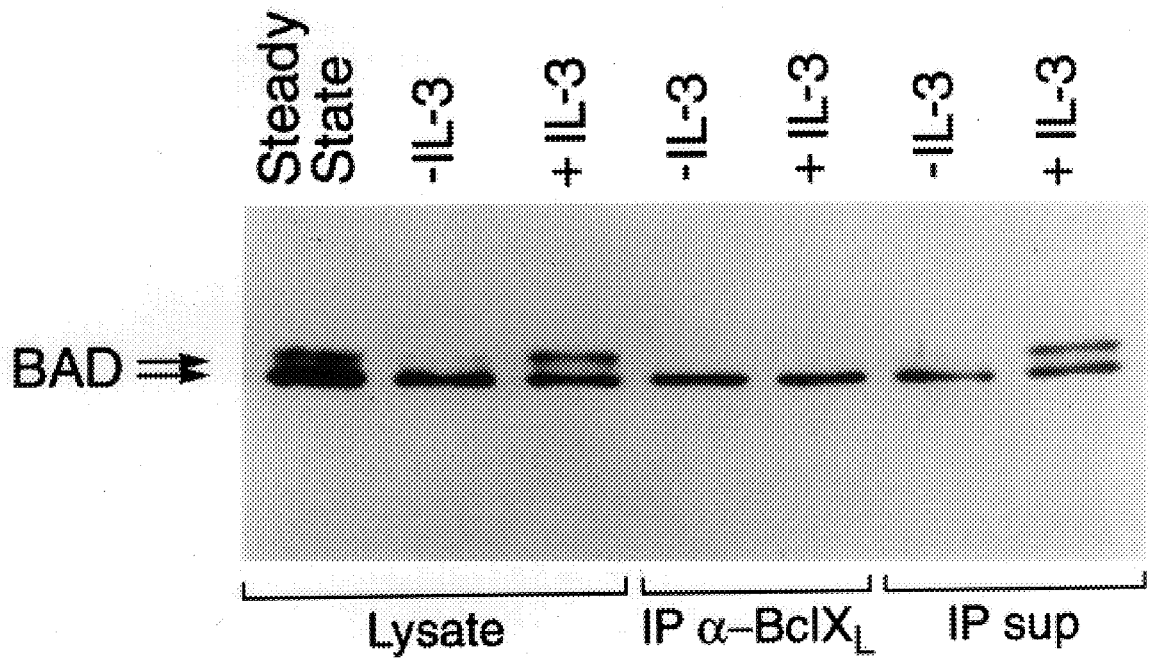
FIG. 4 illustrates an anti-BAD western blot (FIG. 4A) demonstrating the effect of 2 hour IL-3 deprivation and 15 minute IL-3 exposure on BAD hyperphosphorylation and coimmunoprecipitation of a BAD species with anti-BCL-X$_L$ antibody, and (FIG. 4B) showing the effect of kinase activators or kinase inhibitors on BAD hyperphosphorylation status.

Total cell lysates from steady state, two hour IL-3 deprived, and fifteen minute IL-3 exposed cells were analyzed by western blot for the presence of BAD protein using biotinylated rabbit anti-BAD polyclonal antibody 10929. A total cell lysate sample from two hour IL-3 deprived and fifteen minute IL-3 exposed cells were each depleted of BCL-X$_L$ and BCL-X$_L$ complexes by immunoprecipitation with mouse anti-human BCL-X$_L$ antibody. The immunoprecipitated proteins and the remaining proteins in the BCL-X$_L$ depleted samples were analyzed by western blot for the presence of BAD protein as above. Two hours following withdrawal of IL-3, the hyperphosphorylated form of BAD was almost completely eliminated (FIG. 4a, lane 2). The hyperphosphorylated BAD species becomes prominent within fifteen minutes after readdition of IL-3 (FIG. 4a, lane 3). Immunoprecipitation of BCL-X$_L$ and BCL-X$_L$ complexes coprecipitated only the lower form of BAD (FIG. 4a, lane 4), even when the hyperphosphorylated form of BAD was prominent (FIG. 4a, lane 5). Analysis of total cell lysate samples depleted of BCL-X$_L$ by immunoprecipitation confirmed that the hyperphosphorylated BAD species was present there. This indicated that the hyperphosphorylated form of BAD was unable to associate with BCL-X$_L$.

Figure 4B:
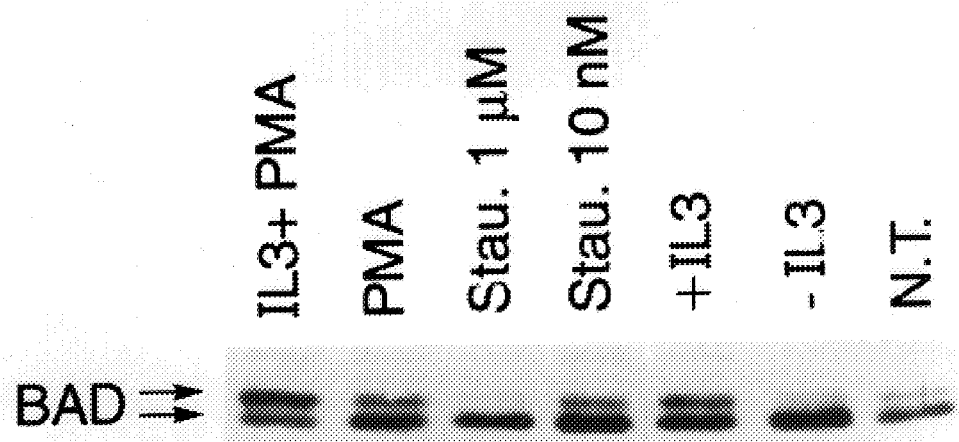

Kinase activators and inhibitors were tested to determine their effects on the rapid phosphorylation of BAD upon readdition of IL-3. FL5.12 cells co-expressing BCL-X$_L$ and BAD were examined after two hours of IL-3 deprivation or fifteen minutes after readdition of IL-3. Readdition of IL-3 was tested alone or included with 10 nM or 1 µM Staurosporine (a kinase inhibitor), or with 10 nM PMA (4-phorbol-12-myristate 13-acetate, a kinase activating phorbol ester). Cell samples were removed and whole cell lysates were analyzed by western blot for the presence of BAD using a biotinylated anti-BAD antibody 10929. Treatment with PMA in the absence of IL-3 caused a shift of BAD to the hyperphosphorylated form (FIG. 4b, lane 2) and enhanced the hyperphosphorylation in the presence of IL-3 (FIG. 4b, lane 1). In contrast, Staurosporine inhibited BAD hyperphosphorylation which normally follows IL-3 readdition in a dose dependent fashion. This indicates that a kinase is involved in BAD phosphorylation which is activated by PMA and inhibited by Staurosporine.

EXAMPLE 5

This example illustrates that BAD interactions with BCL-X$_L$ or HA14-3-3, and BAD subcellular location are dependent on the phosphorylation status of BAD.

FL5.12 cells coexpressing BCL-X$_L$ and BAD were labeled with $^{35}$S-methionine or with $^{32}$P- or $^{33}$P-orthophosphate as in Example 1. Labeled cells were separated into crude membrane or cytosol fractions as in Example 4, and fractions were immunoprecipitated.

Figure 5A:
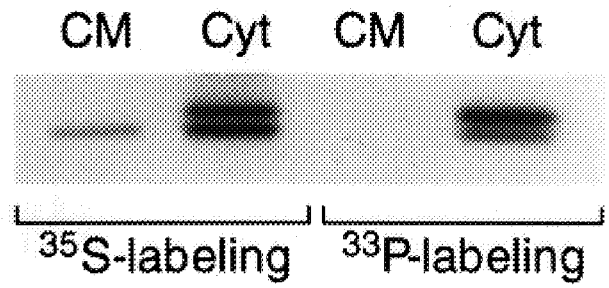
FIG. 5 illustrates (FIG. 5A) an autoradiograph showing in vivo $^{35}$S-methionine labeled anti-BAD immunoprecipitated BAD is localized to the cytosol and to membrane fractions and $^{33}$P-labeled anti-BAD immunoprecipitated BAD is localized to the cytosol, (FIG. 5B) an anti-BAD western blot and an autoradiograph of lysates from $^{32}$P-labeled FL5.12 cells coexpressing BCL-X$_L$ and BAD immunoprecipitated first with anti-BCL-X$_L$ and second with anti-BAD antibody, and (FIG. 5C) an anti-BAD western blot and autoradiograph of hemagglutinin immunoprecipitated proteins from $^{32}$P-labeled FL5.12 cells coexpressing HA14-3-3 and BAD.

BAD protein was immunoprecipitated with anti-BAD 10929 antibody from both fractions and analyzed by autoradiography. The lower $^{35}$S-labeled BAD band was predominantly in the cytosol fraction while some was found within the membrane fraction. All of the $^{35}$S-labeled upper BAD band resided in the cytosol (FIG. 5a, lanes 1 and 2). $^{33}$P-labeled BAD was only observed in the cytosol fraction (FIG. 5a, lane 4), indicating that only non-phosphorylated BAD was found in the membrane fraction while both hypo- and hyperphosphorylated BAD resided in the cytosol.

Figure 5B:
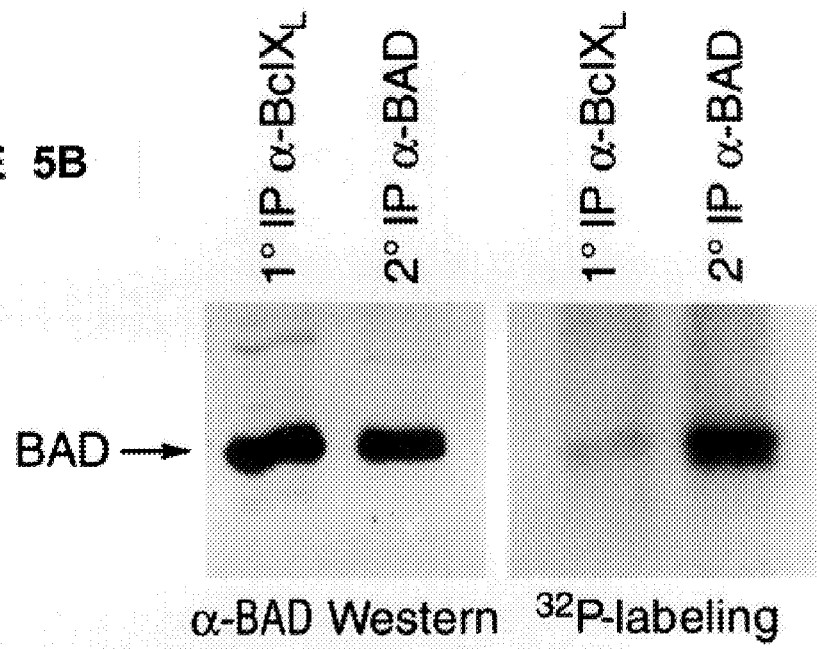

BCL-X$_L$ was immunoprecipitated from whole cell lysates of $^{32}$P-labeled cells with anti-BCL-X$_L$ monoclonal antibody 7B2. These BCL-X$_L$ depleted lysates were then immunoprecipitated with an anti-BAD monoclonal antibody 2G11 as in Example 1. Duplicate samples of each immunoprecipitate were analyzed by western blot for the presence of BAD protein with a biotinylated anti-BAD antibody 10929, or by autoradiography. Immunoblot analysis indicated that about half of the lower BAD band was associated with BCL-X$_L$ (FIG. 5b, lanes 1 and 2) while $^{32}$P-labeled immunoprecipitated protein confirmed that BCL-X$_L$ was only associated with non-phosphorylated BAD (FIG. 5b, lane 3 and 4). Furthermore, immunoprecipitation of a BCL-X$_L$ depleted whole cell lysate with anti-BAD antibody revealed that the portion of BAD not associated with BCL-X$_L$ was comprised of both hypo- and hyperphosphorylated species (FIG. 5b, lane4).

Figure 5C:
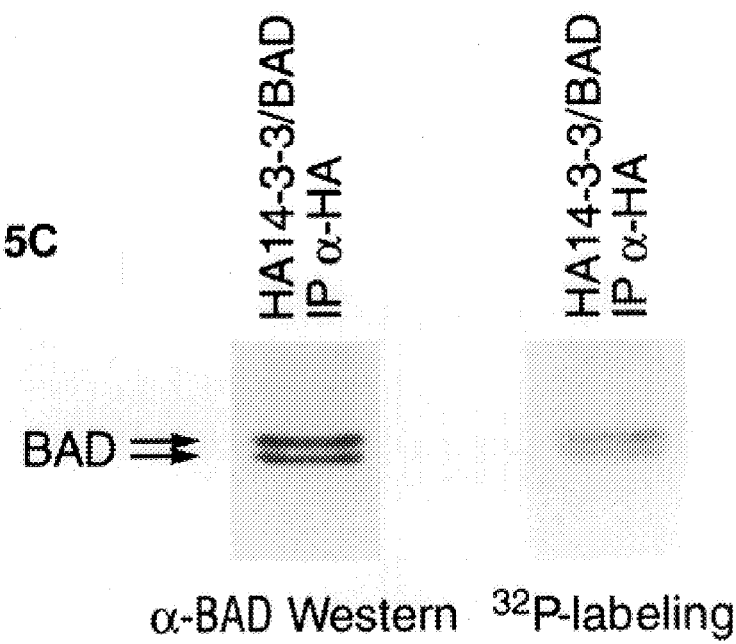

Whole cell lysates of $^{32}$P-labeled FL5.12 cells coexpressing HA14-3-3 and BAD were immunoprecipitated with anti-HA monoclonal antibody 12CA5 as in Example 1, and immunoprecipitates were examined by autoradiography or by immunoblot with biotinylated anti-BAD antibody. Consistent with results in Example 1, immunoprecipitation of HA14-3-3 also extracted both forms of BAD from the total cell lysate (FIG. 5c, lane 1). Examination of $^{32}$P-labeled immunoprecipitates confirmed that HA14-3-3 interacts with both the hypo- and hyperphosphorylated forms of BAD (FIG. 5c, lane 2). Thus, hypo- or hyperphosphorylated BAD is capable of associating with HA14-3-3 within the cytosol, while only non-phosphorylated BAD is capable of associating with membrane bound BCL-X$_L$.

EXAMPLE 6

This example illustrates the serine phosphorylation sites within BAD are within overlapping consensus 14-3-3 binding motifs.

The BAD Ser112 and Ser136 phosphorylation sites reside within RXRXXS as well as overlapping RSXSXP consensus motifs. These sites are compared with the 14-3-3 binding motifs surrounding Ser259 of RAF1, a serine/threonine kinase (FIG. 6). Both motifs have been found at the 14-3-3 binding sites in other proteins (Muslin et al., *Cell* 84:889–897, 1996 which is incorporated by reference). 14-3-3 has been shown to be a motif specific phosphoserine binding protein. BAD Ser112 and Ser136 consensus sites are both homologous to the consensus binding motifs for 14-3-3 defined most critically for RAF1 (Muslin et al., 1996 which is incorporated by reference). BAD Ser136 possesses both the RSXSXP (SEQ ID NO:2) and overlapping RXRXXS (SEQ ID NO:3) motifs found in RAF1 at its 14-3-3 interaction site. However, the BAD Ser112 motif varies at the −2 position with a serine to histidine substitution (RHSSYP (SEQ ID NO:8)), which is also present in tyrosine hydroxylase, a known 14-3-3 binding protein (Furukawa et al., Biochem. Biophys. Res. Comm. 194:144–149, 1993 which is incorporated by reference). Thus, either BAD serine phosphorylation site appears to be capable of mediating binding with 14-3-3.

EXAMPLE 7

This example illustrates a pathway for BAD phosphorylation and binding to 14-3-3.

Figure 7:
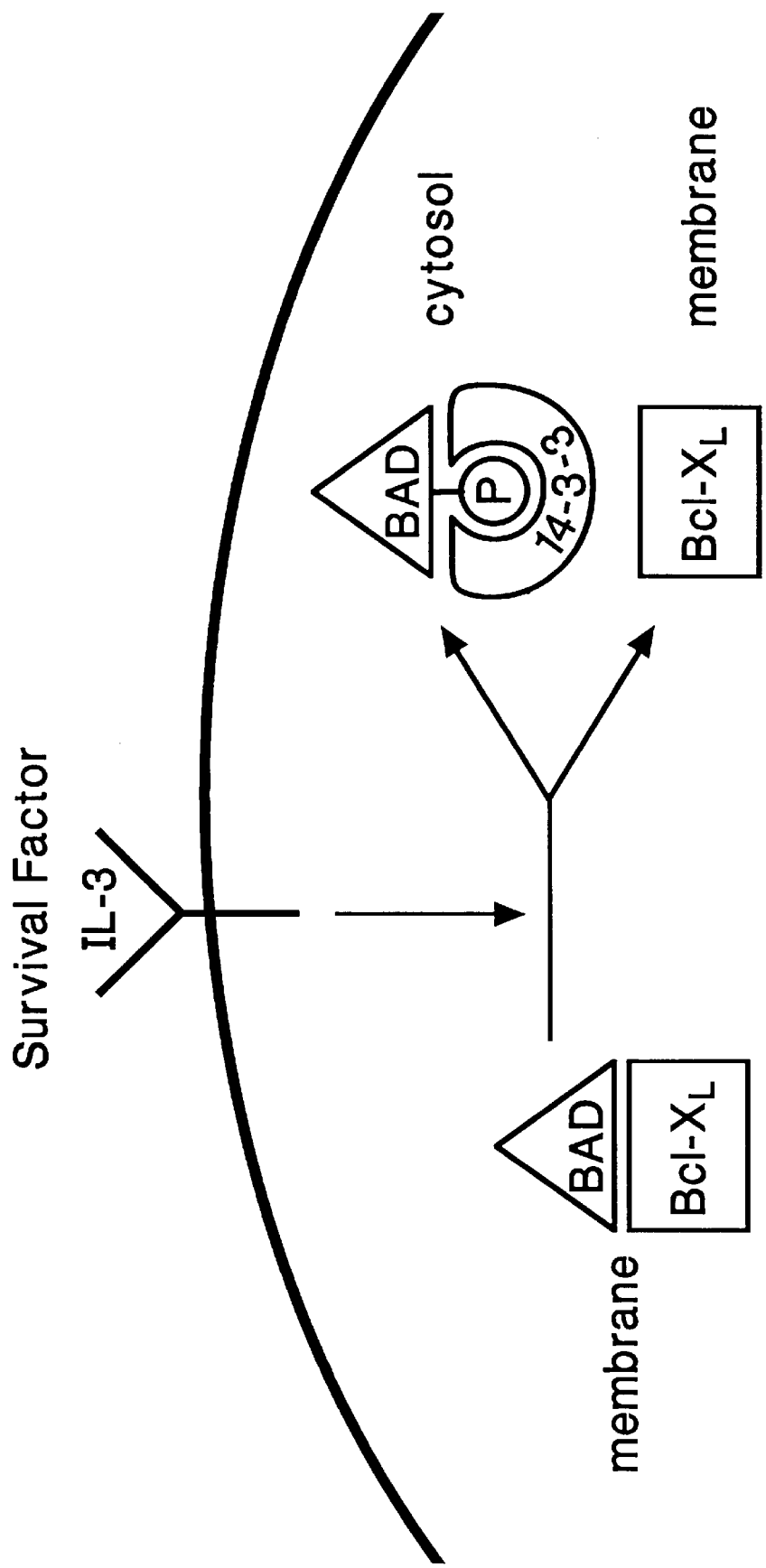
FIG. 7 illustrates a schematic drawing proposing a pathway for BAD/BCL-X$_L$ interaction, IL-3 stimulation of BAD phosphorylation, and interaction of BAD phosphate with 14-3-3 protein.

With reference to FIG. 7, BAD is depicted first as unphosphorylated and bound to BCL-$X_L$, which is bound to an intracellular membrane. IL-3 can bind to the cell, which acts as a survival factor in stimulating the phosphorylation of BAD. Phosphorylated BAD is released from BCL-$X_L$ and is immediately bound by 14-3-3, perhaps to prevent phosphatase activity from removing phosphate from phosphorylated BAD. BCL-$X_L$ remains bound to its membrane. An increase in BCL-$X_L$ which is not bound by BAD promotes survival.

EXAMPLE 8

This example illustrates the binding of non-phosphorylated BAD to BCL-$X_L$ and the lack of binding of phosphorylated BAD to BCL-$X_L$.

Figure 8A:
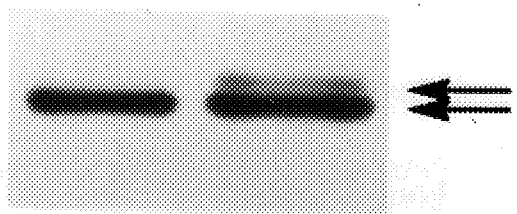
FIG. 8 illustrates (FIG. 8A) an anti-BAD western blot of GST-Bcl-X$_L$ extracted protein from a cell lysate.
(FIG. 8B) an anti-BAD western blot of GST-Bcl-X$_L$ extracted non-phosphorylated BAD, and an autoradiograph of in vitro [$^{32}$p] labeled BAD protein remaining after GST-Bcl-X$_L$ extraction.

FL5.12 cells expressing BAD were lysed as in example 1. Purified GST-BCL-$X_L$ was used to capture BAD protein from the supernatant fraction of these cell lysates. The GST-BCL-$X_L$/BAD protein complexes and residual proteins in samples of GST-BCL-$X_L$ depleted supernatant were subjected to Western blot analysis and developed with polyclonal anti-BAD antibody (10929). Only the lower BAD species was extracted from supernatants by GST-BCL-$X_L$, while hyperphosphorylated BAD remained in the depleted fraction (FIG. 8a). However, only about half of the lower BAD species was extracted from the supernatants by GST-BCL-$X_L$.

Figure 8B:
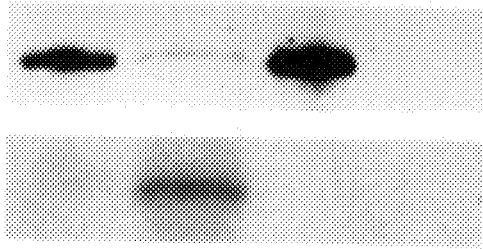

Bad cDNA was cloned into the BamHI site in frame with the histidine tag leader sequence in pET-14b (Novagen Inc.). The resulting plasmid was designated pET-14b-Bad. Histidine-tagged BAD was expressed in E. coli and purified according to instructions from Novagen. The histidine leader sequence was cleaved to release purified BAD protein. Samples of the purified BAD protein were phosphorylated in vitro by heart muscle kinase (HMK) and [$^{32}$P]-ATP at Ser112. HMK treated-[$^{32}$P] labeled BAD and untreated BAD were incubated with GST-Bcl-$X_L$. GST-BclX$_L$/BAD complexes were captured by GSH-agarose. Captured complexes and soluble fractions were analyzed by western blot with anti-BAD antibody (10929) and by autoradiography. All of the non-phosphorylated BAD bound entirely to GST-Bcl-$X_L$ (FIG. 8b, top panel, lanes 3 and 4). Phosphorylated BAD was detected only in the soluble fraction, indicating that phosporylated BAD species could not bind to GST-Bcl-$X_L$ (FIG. 8b, lower panel, lanes 1 and 2).

EXAMPLE 9

This example illustrates the binding to 14-3-3 and the increased death agonist activity of mutant BAD polypeptides having alanine residues in positions 112 and/or 136 compared to the naturally occurring BAD polypeptide which has serine residues in the same positions.

Figure 9A:
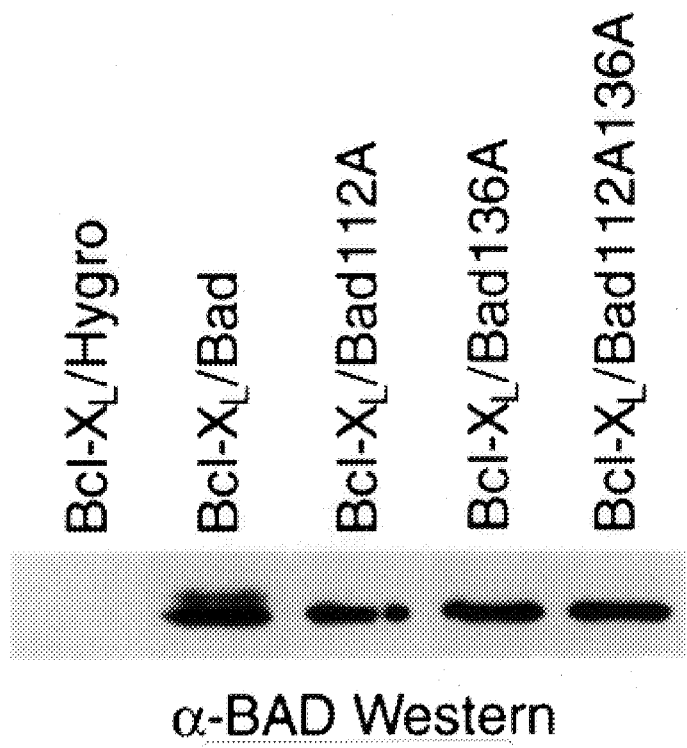
FIG. 9 illustrates (FIG. 9A) an anti-BAD western blot of cell lysates from cells expressing BAD polypeptide or serine substituted mutant polypeptides (BAD 112A, containing alanine in position 112, SEQ ID NO:12; BAD 136A containing alanine in position 136, SEQ ID NO:13; and BAD 112A136A containing alanine in positions 112 and 136, SEQ ID NO:14)
(FIG. 9B) an anti-14-3-3 western blot of anti-BAD antibody coprecipitated BAD polypeptide and serine substituted mutant polypeptides.
(FIG. 9C) death agonist activity in cells expressing BAD polypeptide and serine substituted mutant BAD polypeptides measured as percent viability.

Bad cDNA was cloned into the EcORI site of pSSFV. The BAD coding sequence was altered using a PCR-based site directed mutagenesis kit (Stratagene, Inc.) and synthetic oligonucleotides which incorporated serine to alanine codon substitutions (Ser112Ala, 5'-GCG TAC CCA GCG GGG ACC GAG-3', SEQ ID NO:59; Ser136Ala, 5'-GCG GCT CCC CCC AAT CTC TGG-3', SEQ ID NO:60). Substitutions resulted in Ser112 (TCG) to Ala112 (GCG) or Ser136 (TCG) to Ala136 (GCG). A set of four plasmids were constructed so that a wild type BAD and three mutant BAD proteins could be expressed. Mutants were referred to as Bad112A, Bad136A, and Bad112A136A, representing the possible substitutions of alanine for serine at these amino acid positions. Independent sets of FL5.12 Bcl-$X_L$ stable clones expressing comparable levels of wild type BAD, BAD112A, BAD136A, or BAD112A136A were generated. Clones were compared by western blot developed with an anti-BAD antibody (10929) for relative levels of BAD protein expression. The hyperphosphorylated band was not detected in any of the mutant clones, confirming that the upper BAD species was the result of BAD phosphorylation at Ser112 and Ser136 (FIG. 9a).

Figure 9B:
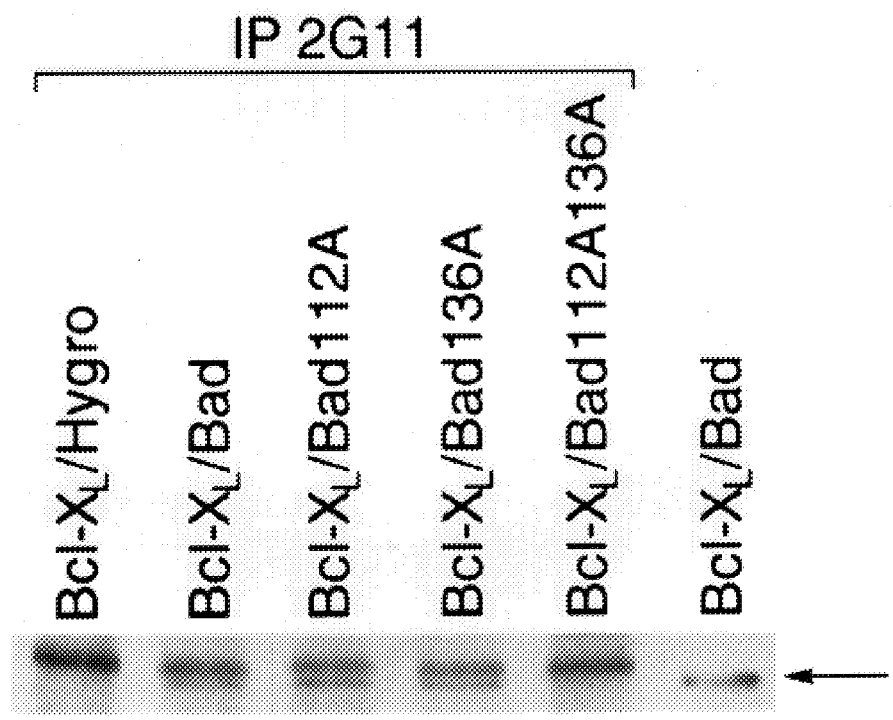

Serine 112 and serine 136 lie within consensus 14-3-3 binding domains. Lysates of FL5.12 Bcl-$X_L$ clones which express wild type or serine substituted mutant forms of BAD were immunoprecipitated with a monoclonal anti-BAD antibody (2G11). Immunoprecipitates were analyzed by western blot to detect the presence of 14-3-3 coprecipitating with BAD. Blots were developed with a polyclonal anti-14-3-3 antibody (Dr. Andre Shaw, Washington University, St. Louis, Mo.). The results reveal that either consensus binding site is independently capable of binding 14-3-3 when the serine residue is present (FIG. 9b, lanes 3 and 4). However, 14-3-3 did not coprecipitate with the double mutant BAD112A136A, indicating that phosphorylation of these serine residues is responsible for 14-3-3/BAD interactions.

Figure 9C:
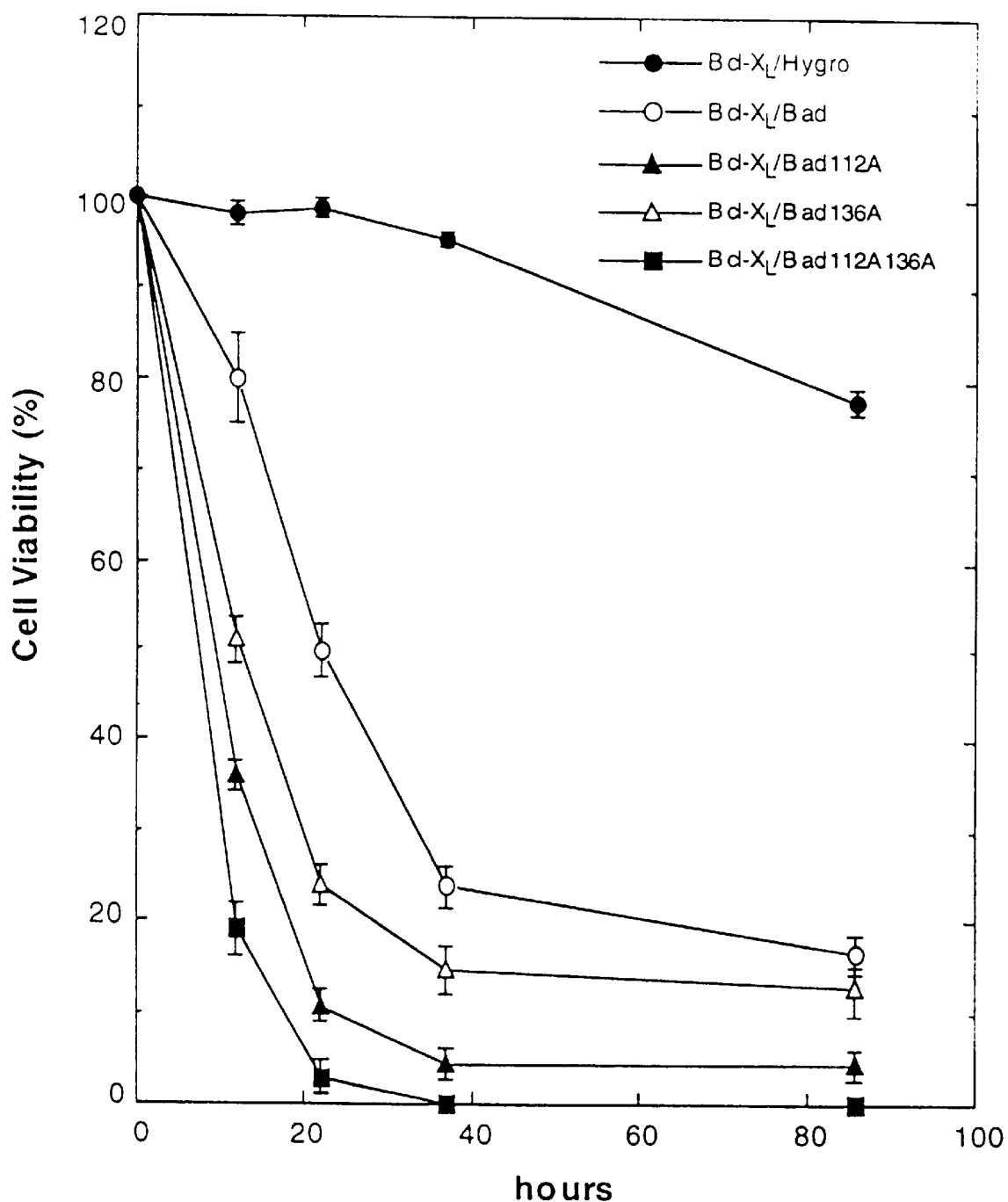

FL5.12 Bcl-$X_L$ stable clones which express comparable levels of wild type or serine substituted forms of BAD were deprived of IL-3 and assessed for viability. The fraction of viable cells was assessed at various times after IL-3 deprivation by trypan blue exclusion. Each of the serine substituted BAD proteins demonstrated a stronger death agonist activity than wild type BAD. BAD112A136A, which does not bind 14-3-3, provided the strongest death agonist activity (FIG. 9C).

In view of the above, it will be seen that the several advantages of the invention are achieved and other advantageous results attained.

As various changes could be made in the above methods and compositions without departing from the scope of the invention, it is intended that all matter contained in the above description and shown in the accompanying drawings shall be interpreted as illustrative and not in a limiting sense.

What is claimed is:

1. An isolated polypeptide comprising an amino acid sequence of a mutant BCL-X$_L$/BCL-2 associated cell death regulator (BAD) polypeptide, wherein said amino acid sequence is identical to that of a naturally-occurring mammalian BAD polypeptide except for having an amino acid other than serine at one or both of first and second positions corresponding to position 112 and position 136 of SEQ ID NO:1, said first and second positions being identified by alignment of said amino acid sequence to SEQ ID NO:1, wherein said naturally-occurring mammalian BAD polypeptide (a) contains a BH1 domain comprising residues 142 to 152 of SEQ ID NO:1 and (b) contains a BH2 domain, and wherein said mutant BAD polypeptide has cell death agonist activity.

2. The polypeptide of claim 1, wherein said naturally occurring mammalian BAD polypeptide comprises SEQ ID NO:1 or SEQ ID NO:55.

3. The polypeptide of claim 2, wherein the amino acid other than serine at one or both of said first and second positions is alanine.

4. The polypeptide of claim 3, wherein said amino acid sequence is SEQ ID NO:12, SEQ ID NO:13, or SEQ ID NO:14.

5. The polypeptide of claim 3, wherein said amino acid sequence comprises SEQ ID NO:56, SEQ ID NO:57, or SEQ ID NO:58.

6. An isolated polypeptide comprising a fragment of said mutant BAD polypeptide of claim 1, wherein said fragment comprises the BH1 domain, the BH2 domain and at least one of said first and second positions which is an amino acid other than serine, wherein said fragment has cell death agonist activity.

7. The fragment of claim 6 which comprises both of said first and second positions with each position being an amino acid other than serine.

8. The fragment of claim 6, wherein said mutant BAD polypeptide consists of SEQ ID NO:12, SEQ ID NO:13, or SEQ ID NO:14.

9. The fragment of claim 6, wherein said mutant BAD polypeptide comprises SEQ ID NO:56, SEQ ID NO:57, or SEQ ID NO:58.

10. A method for making a mutant BCL-$X_L$/BCL-2 associated cell death regulator (BAD) polypeptide which has cell death agonist activity, the method comprising (a) selecting an amino acid sequence of a naturally occurring mammalian BAD polypeptide which (1) contains a BH1 domain comprising residues 142 to 152 of SEQ ID NO:1, (2) contains a BH2 domain, and (3) contains serine residues at first and second positions corresponding to positions 112 and 136 of SEQ ID NO:1, said first and second positions being identified by alignment of said amino acid sequence to SEQ ID NO:1, (b) preparing said mutant BAD polypeptide, said mutant BAD polypeptide containing said amino acid sequence except for an amino acid other than serine at one or both of said first and second positions; and (c) testing said mutant BAD polypeptide for cell death agonist activity.

11. The method of claim 10, wherein said amino acid other than serine is alanine.

12. The method of claim 11, wherein said amino acid sequence is SEQ ID NO:1.

13. The method of claim 12, wherein the mutant BAD polypeptide consists of SEQ ID NO:12, SEQ ID NO:13 or SEQ ID NO:14.

14. The method of claim 11, wherein said amino acid sequence comprises SEQ ID NO:55.

15. The method of claim 14, wherein the mutant BAD polypeptide comprises SEQ ID NO:56, SEQ ID NO:57 or SEQ ID NO:58.

16. The method of claim 10, wherein said preparing step comprises expressing the mutant BAD polypeptide in a host cell transformed with a polynucleotide encoding the mutant BAD polypeptide.

17. The method of claim 16, wherein said polynucleotide comprises SEQ ID NO:16, SEQ ID NO:17 or SEQ ID NO:18.

18. The method of claim 16, wherein said polynucleotide comprises SEQ ID NO:52, SEQ ID NO:53 or SEQ ID NO:54.

* * * * *